(12) United States Patent
Kirsner

(10) Patent No.: US 7,427,271 B2
(45) Date of Patent: Sep. 23, 2008

(54) DIAGNOSIS OF FERTILITY STATUS BY FOLLICULOGENESIS MONITORING IN THE VAGINA

(76) Inventor: Vaclav Kirsner, 83 Davis Ranch Rd., Bellvue, CO (US) 80512

( * ) Notice: Subject to any disclaimer, the term of this patent is extended or adjusted under 35 U.S.C. 154(b) by 218 days.

(21) Appl. No.: 10/610,175

(22) Filed: Jun. 30, 2003

(65) Prior Publication Data
US 2005/0165326 A1    Jul. 28, 2005

(51) Int. Cl.
A61B 10/00    (2006.01)
A61B 5/00     (2006.01)
A61B 5/04     (2006.01)
A61B 5/05     (2006.01)
A61B 5/103    (2006.01)
A61B 5/117    (2006.01)

(52) U.S. Cl. .................. 600/551; 600/300; 600/306; 600/546; 600/554; 600/587; 600/591

(58) Field of Classification Search .......... 600/551, 600/300, 306, 546, 554, 587, 591
See application file for complete search history.

(56) References Cited

U.S. PATENT DOCUMENTS

| | | | | |
|---|---|---|---|---|
| 3,749,089 A | * | 7/1973 | Derr | 600/345 |
| 3,844,276 A | * | 10/1974 | McDougall | 600/373 |
| 4,224,949 A | * | 9/1980 | Scott et al. | 600/373 |
| 4,292,315 A | * | 9/1981 | Vorys | 514/178 |
| 4,557,273 A | * | 12/1985 | Stoller et al. | 600/551 |
| 4,660,567 A | * | 4/1987 | Kaneko et al. | 600/459 |
| 4,685,471 A | * | 8/1987 | Regas et al. | 600/547 |
| 4,753,247 A | | 6/1988 | Kirsner | |
| 4,770,186 A | | 9/1988 | Regas et al. | |
| 4,784,155 A | * | 11/1988 | Mills | 600/547 |
| 4,815,835 A | * | 3/1989 | Ortueta Corona | 359/379 |
| 4,836,216 A | | 6/1989 | Fernando et al. | |
| 4,931,403 A | * | 6/1990 | Cutler et al. | 436/65 |
| 5,109,865 A | * | 5/1992 | Matsuura | 600/551 |

(Continued)

OTHER PUBLICATIONS

S.J. Segal, in E.E. Wallach and H.A. Zacur, editors: Reproductive Medicine and Surgery, Mosby, 1995.

(Continued)

Primary Examiner—Max Hindenburg
Assistant Examiner—Jeffrey G Hoekstra
(74) Attorney, Agent, or Firm—Craig Miles; CR Miles, P.C.

(57) ABSTRACT

Methods and apparatus for interpreting vaginal measurement data by electronic means without the need for the user to take part in the data interpretation process. More specifically, an intelligent probe monitors folliculogenesis and correlates the ovarian function data to probe profile characteristics of the female reproductive cycle. A fertile window is defined with reference to the correlation between folliculogenesis and probe cyclic profiles. Data stored within the apparatus can be downloaded into an external display appliance or data analysis unit. Another aspect of the invention allows for continuous layout of the memory of preceding cycles in the inventory of the apparatus, retaining the most recent while erasing the most distant stored data. These methods assure a reliable fit for the diagnosis of fertility, treatment of infertility as far as timing of treatment procedures, management of subfertility and other gynecological disorders such as luteal phase deficiency or short luteal phase, and the management of premenstrual mood disorders, and of premenopausal and menopausal patients.

4 Claims, 17 Drawing Sheets

U.S. PATENT DOCUMENTS

| | | | | |
|---|---|---|---|---|
| 5,137,028 | A | * | 8/1992 | Nishimura .................. 600/551 |
| 5,151,344 | A | * | 9/1992 | Abe et al. .................. 430/383 |
| 5,209,238 | A | * | 5/1993 | Sundhar .................... 600/551 |
| 5,216,599 | A | * | 6/1993 | Uebe et al. ................. 600/551 |
| 5,240,010 | A | * | 8/1993 | Weinmann .................. 600/547 |
| 5,515,344 | A | | 5/1996 | Ng |
| 5,916,173 | A | * | 6/1999 | Kirsner ....................... 600/551 |
| 6,174,290 | B1 | * | 1/2001 | Cho ........................... 600/551 |
| 6,364,844 | B1 | | 4/2002 | Regas et al. |
| 2002/0103106 | A1 | * | 8/2002 | Palmer et al. ................. 514/1 |
| 2002/0156394 | A1 | * | 10/2002 | Mehrotra et al. ............ 600/551 |

OTHER PUBLICATIONS

J. Hotchkiss and E. Knobil in E.Y. Adashi, J.A. Rock and Z. Rosenwaks, editors: Reproductive Endocrinology, Surgery and Technolgy, Lippincott-Raven Publishers, 1996.

C.J. Verco, in A.M. Siegler, editor: The Fallopian Tube. Basic Studies and Clinical Contributions, Futura Publishing Company, 1986.

C. Owman et al., idem. 1986.

Dr. L. Shettles, "How to Choose the Sex of Your Baby", Doubleplay, 1989.

S. Anand, in A.M. Seigler, editor: The Fallopian Tube, Futura Publishing Company, 1986.

B.M. Sanborn et al., J. St. Biochem. 9:951, 1978.

G.I. Gorodeski et al., din. Endocrinol. Metab. 70:1624, 1990.

G. Fried et al., Human Reprod. 5:870, 1990.

G.I. Gordeski et al., Fertil. Steril. 47:108, 1987.

A.L. Goodman G.D. Hodgen, in R.O. Greep, editor: Recent progress in hormone research, Academic Press. 1983.

G.D. Hodgen, Fertility and Serility 38:28 1, 1983.

A.J. Zeleznik, in E.Y. Adashi and P.K.C Leung, editors: The Ovary, Raven, 1993, pp. 41-45.

G.F. Erickson in J. Shoemaker and R. Schats, editors: Ovarian Endocrinopathies, Parthenon, 1994, pp. 103-115.

E.L. Nestor et al, J. Chin. Endocrinol. Metab. 77:439,1993.

E.Y. Adashi, J.A. Rock, and Z. Rosenwaks, editors: Reproductive Endocrinology, Surgery, and Technology, Lippincott-Raven Publishers, 1996.

S.K. Smith et al., J. Reprod. Fert. 75:363, 1985.

W.F. Gangong, Review of Medical Physiology, 17$^{th}$ edition, Appleton & Lange, 1995, Chapter 23.

* cited by examiner

DIAGNOSIS OF FERTILITY STATUS BY FOLLICULOGENESIS MONITORING IN THE VAGINA

BACKGROUND OF THE INVENTION

1. Field of the Invention

The present invention generally concerns the field of intelligent medical diagnostic devices. The present invention particularly concerns an apparatus and method for interpretation by electronic means of the meaning of vaginal measurement data without the need for the user to take part in the data interpretation process, and for optional downloading of the data stored within the apparatus into an external display appliance or data analysis unit. The apparatus and method are particularly useful as an aid for the management of female patients with reduced fertility or infertility, and as a tool for natural or scientific family planning approach to birth control.

2. Description of the Related Prior Art

2.1 General Background and Problems with Competition Methods

The background of the invention of this application includes the more than 3 million unintended pregnancies that occur annually in the U.S., about half of which are attributable to contraceptive failure. The U.S. population of women that use some form of birth control comprises approximately 30 million to 40 million women. "There is no surer way to reduce the number of abortions in the U.S. and throughout the world than by improving the effectiveness of contraception" [S. J. Segal, in E. E. Wallach and H. A. Zacur, editors: Reproductive Medicine and Surgery, Mosby, 1995]. Worldwide, there has been a tenfold increase in the use of birth control over the last 3 decades, the numbers exemplified by the almost 400 million of contraceptive users in the developing world (in 1994), and by the more than 50% of couples in the reproductive age group that practice birth control. In this context, the use of the so-called natural family planning method is increasing for a number of reasons, including cost-effectiveness, health and religious considerations. Against the baseline statistics of a mere 10% to 20% chance of conception from an unprotected intercourse for a normal healthy couple in any given month, the high incidence and increasing trend of infertility (approximately 20% in the U.S.) is the other side of the background of this invention. Infertility treatment is crucially dependent on timing of procedures with respect to ovulation, and on individualized procedures with careful monitoring.

On the basic level of the art, the issue or problem is how to detect one or more reliable indicators of the fertility status which is infertile except for a few days at the so-called midcycle. The present application addresses the next level which is how to utilize such diagnostically useful information in a user-friendly and reliable manner so as to make it possible for the user to obtain directly the diagnostic decision on whether fertile (conception can occur) or not fertile (conception cannot physically occur), without obligating the user to make any decisions on how to interpret the measurement data. The apparatus according to the inventions of this application performs this data interpretation automatically. The methods used for the electronic probe data interpretation stem from a new understanding of the chronobiological meaning of the probe cyclic profile and of its individual features. This results in a method of assessing the periodic development of the egg in its protective microscopic sack (called the follicle) as a function of at least two biological pacemakers or "clocks".

One competitor that attempts to serve the purpose of electronic interpretation of certain kinds of fertility data is the Persona electronic colorimeter for urine analysis from Unipath Ltd. of Britain. It consists of detecting, in a woman's urine, both the luteinizing hormone (LH) surge that typically marks the ovulation day, as well as a metabolite of estrogen, i.e., another hormone which anticipates by about one day the luteinizing hormone surge. Since, unlike my probe, the Persona depends on biochemical reagents and since the supply of the reagents is limited, the user needs to estimate on which day of her menstrual cycle she should start using the system. She does that based on her history of menstrual cycles as though the length and the timing of the present menstrual cycle were the same as in her previous cycles. Because of variable lengths of successive cycles in most women, this is a weak feature in the design of the Unipath system. Even more significantly, this weakness is also involved in its ovulation-predicting method, which is based on data pooled from other women and on the user's estrogen and LH data history, if available, both stored in the Persona's memory.

The Persona Contraceptive System of Unipath Ltd. is an attempt at an improvement upon the commercially available luteinizing hormone (LH) kits that only aim to detect the LH surge in the woman's urine. Two beneficial features have been introduced by Unipath Ltd.: 1. the addition of an estrogen metabolite to the diagnostic measurement so as to anticipate the LH surge, and 2. the measurement is performed instrumentally rather than as a subjective judgment of a color change by the woman-user. However, ovulation as such is not detected by the Persona device. Ovulation is, in fact, known to fail to occur in approximately 20% of the follicles that, triggered by the LH, undergo the cyclic event of follicle rupture. Ovulation also fails to occur with another type of follicles, the so-called luteinized unruptured follicles. Yet, the LH surge can be seen in either case and is therefore a false indicator.

One other problem of the Persona is that the urinary concentration of the estrogen metabolite E3G peaks only within 24 hours prior to the LH surge. This is not at all early enough to serve as a marker of the beginning of the fertile phase. The Unipath literature states that "a sustained rise in E3G can be used to identify the start of the fertile phase", referring to a slow gradual increase that eventually becomes the peak of E3G concentration. While the Unipath Persona Personal Contraceptive System has been introduced to the market in Britain, the statistical testing for its reliability is still in progress. The attempt by Unipath to use an ill-defined rise rather than the peak in the cyclic profile of the estrogen metabolite is not a viable solution. Even if the ill-defined E3G rise in the urine were correlated with a clearly defined early stage of egg development towards ovulation, a serious flaw of the Unipath method is their reliance on pooled, rather than actual single-event, data in defining the start of the fertile period in a given cycle.

The gradual increase of the E3G concentration in the urine, proceeding at different rates in different cycles, can hardly be predictably associated with the beginning of the fertile period. Estrogen is known to have both stimulatory and inhibitory effects on LH secretion and, to be effective as a stimulant, must rise to its peak levels (>150 to 200 pg/mi) and must remain elevated for at least 36 hours [J. Hotchkiss and E. Knobil in E. Y. Adashi, J. A. Rock and Z. Rosenwaks, editors: Reproductive Endocrinology, Surgery and Technology, Lippincott-Raven Publishers, 1996]. The E3G profile does not reflect the local interplay with progesterone but only reflects clearance of one of at least 10 metabolites of estrogen from peripheral blood circulation into the urine after oxidative conversion in the liver. Whatever the rate of this clearance process, there are local mechanisms due to which the quantification of ovarian steroids in peripheral blood or in urine is rendered "interesting but of little value in predicting the genital end-organ effect" [C. J. Verco, in A. M. Siegler, editor: The Fallopian Tube. Basic Studies and Clinical Contributions, Futura Publishing Company, 1986].

Ovarian vein-to-artery exchange of steroids, prostaglandins and other bioactive substances is a local transfer mechanism. As such, it enables local regulation of ovarian, tubal and uterine functions, with genital organs therefore exposed at any given time to hormonal concentrations that are higher than the peripheral concentrations. This kind of acute exposure is of particular relevance to the regulation of the physiology of the genital organs. The local, as opposed to peripheral, blood concentrations of the steroid hormones are also believed to control the innervation of the female genital tract. The cervix, like the isthmus region of the fallopian tube, has a particularly dense innervation by, for example, the vasoactive intestinal polypeptide nerve [C. Owman et al., idem.]. These examples of local and acute regulatory mechanisms remain undetected by the prior art techniques that focus on peripheral variables. Such peripheral or systemic techniques then resort to pooled, averaged, data as though synchronization of menstrual cycles were somehow present.

The flawed assumption of similar timing of menstrual cyclic events from one cycle to another has been a problem for the microprocessor controlled thermometers. Since the late sixties, the microprocessor technology has been applied by a number of people to the well-tried basal body temperature approach to family planning. These products are not recognized as medically valid even if they may be acceptable to some of the older physicians. This is because of the fact that the so-called basal body temperature (BBT) is a systemic variable or a secondary parameter that reflects, among other things, progesterone rise in blood after ovulation, usually one or two days later. Even though in some women in some cycles a dip in the temperature graph may be observed one day before the post-ovulatory temperature rise, it is clear that the BBT method is of little value due to its lack of predictive capability and due to its fundamental unreliability.

Another electronic fertility monitor that did attempt to anticipate ovulation was the Cue fertility monitor from Zetek. It consisted of two resistivity sensors: one oral (to detect a change in resistivity of saliva in the mouth some 5 or 6 days before ovulation), and one vaginal (to detect a change in resistivity of the mucus in the vagina, marking ovulation). The Cue monitor measured the concentration of electrolytes, particularly common salt, in the saliva and in vaginal mucus. These are remote indicators of the physiological changes that are associated with the fertility status of the cervical uterine tissues. The Cue monitor was unreliable and it did not provide for a distinction between fertile versus not fertile days. It was also cumbersome to use, expensive, and not at all feminine in any sense.

The inability to predict ovulation is inherent in U.S. Pat. No. 5,209,238 (Sundhar, May 11, 1993) which purports to determine empirically the presence of a viable egg by detecting the simultaneously elevated readings of four vaginal measurements. The measured parameters are the basal body temperature (BBT), the concentration of luteinizing hormone (LH) postulated to be present on the vaginal wall surfaces, the alkalinity of cervical mucus (pH), and the viscosity of cervical mucus detected as an increased pressure (p) on a thin diaphragm. The presence of a viable egg is defined by Sundhar as all four parameters registering above respective threshold values which his patent leaves unspecified.

Sundhar states that the cervical fluid, which provides for the elevated values of pH and p, appears at the mouth of the cervix only after the rupture of the follicle. He states that the alkalinity and the density of the mucous fluid are "the determining factors of ovulation". He does acknowledge the fact that the BBT becomes elevated only about 24-48 hours after the rupture of the follicle to which he assigns its origin. He also appears to recognize that LH levels, on the other hand, peak some 18 hours before the event which means that by the time ovulation occurs, the LH is back to low levels. Regardless of whether he therefore works with parameters that do not, in fact, change at the time of ovulation and whether or not they change simultaneously to justify his definition of the presence of a viable egg, the fact is that there is no capability to anticipate ovulation by several days with his method and apparatus. Neither does his patent define the end of the fertile period (which in his terminology would be 'viable egg no longer present'). The Sundhar patent does neither address nor satisfy the need for the determination of the window of fertility even if it does seek a correlation between several parameters associated with the menstrual cycle. Sundhar does not include the day of cycle among his set of parameters.

In contrast, Weilgain Precision Products Ltd. of Hong Kong have a U.S. Pat. No. 5,515,344 (Ng, May 7, 1996) teaching a menstrual cycle meter that is a microprocessor-based calendar which basically provides for the day of cycle as the tracked parameter. The so-called menstrual cycle meter calculates the fertile and infertile periods of the current menstrual cycle based on at least two previous cycle lengths and the respective first days of the cycles. The apparatus purports to indicate the expected sex of a baby that is likely to be conceived on any given day during the calculated fertile period. This purpose of the Ng menstrual cycle meter may be controversial and the method is fundamentally flawed but the patent filed from Hong Kong may also be taken as evidence of public interest in fetal sex pre-selection in the context of small family planning.

In the U.S., this topic is often associated with Dr. L. Shettles, the author of the book "How to Choose the Sex of Your Baby" [Doubleday, 1981]. According to "Dr. Shettles Method", the critical variable for fetal sex preselection is the timing of intercourse with respect to ovulation. Briefly, and without necessarily subscribing to it, I would note that the method teaches that, to aim for a boy, intercourse should be timed to occur on the day of ovulation or the day after; the more difficult to pre-select female gender is to be aimed at by timing intercourse "several days before ovulation but preferably not closer than two days before". It will be clear from the description below that the intelligent probe of the present invention is eminently suited to be a timing tool in such a process.

The menstrual cycle meter of Ng is related to the Shettles Method. The problem with the Ng invention is that it relies on the old, failed, calendar or rhythm method of birth control. The method had failed in terms of its high contraceptive failure rate resulting from its assumption of similar timing of menstrual cyclic events from one cycle to another, one of the fundamental flaws discussed above in connection with the other prior art.

The erroneous assumption that women usually have 28-day cycles and that they ovulate on day 14 may cause problems even outside of the arena of fetal sex-preselection. Problems can occur in standard monitoring of pregnancy, if relying on the method or the date of the so called pregnancy wheel. Indeed, miscalculations of the expected date of delivery, in the absence of diagnostic means such as ultrasound, have even led to the induced labor of many premature babies. It will be clear, from the description that follows, that the present invention has useful applicability also in pregnancy planning.

Weinmann's U.S. Pat. No. 5,240,010 (Weinmann, Aug. 31, 1993), filed from Israel, is another piece of evidence that electronic interpretation of multiple input data related to fertility does not necessarily lead to a meaningful acceptable solution of the problem posed by the need to anticipate fertility status changes, including the need to predict ovulation. Merely processing a multitude of inadequate data inputs, in the hope that synergistically they may achieve adequate fertility prediction, does not do the job even if one of the inputs is some vaginal impedance parameter. Weinmann's other inputs are vaginal temperature in lieu of the BBT for the end of the fertile period, and a rhythm method calculation for the beginning of the fertile period.

2.2 The Need to Monitor Folliculogenesis

Monitoring of ovarian function is absent in competitors' prior art. What is missing in the cited prior art is a specific link between the employed indicators and the events that occur well before ovulation, that is the link with specific early stages of ovarian function. Ovarian function in every menstrual cycle involves the formation and maturation of the dominant follicle in the ovary, followed by the follicle rupture and the release of the egg (ovulation). Moreover, the prior art of the competitors does not work with the various biological pacemakers (such as in particular the circamensual and the circhoral "clocks") that are inherently involved in my present patent application. To be sure other pacemakers exist in the reproductive system, including, significantly, one in the oviducts or fallopian tubes [S. Anand, in A. M. Siegler, editor: The Fallopian Tube, Futura Publishing Company, 1986], and they are all likely to be involved in the dominant follicle's prerogative to synchronize them (vide infra, this section).

Ovarian function and its significance for the invention cannot be understood without consideration of the fact that there are other endocrine organs that communicate stimulatory or inhibitory signals to the ovary and to which the ovary feeds back its signals. Since in this manner there is a connection between the hypothalamus and the pituitary gland of the brain and the two ovaries, this connection is called the hypothalamic-pituitary-ovarian axis.

The mediators of communication among the organs are certain hormones released into the blood circulation. As indicated in section 2.1, it is some of these mediator compounds that the competitors' prior art targets, directly or even indirectly, as the handle on the timing of the menstrual cycle. Briefly, the peptide follicle-stimulating hormone (FSH), released by the pituitary, primarily functions to induce proliferation of the follicular granulosa cells in one of the two ovaries and to stimulate an aromatase enzyme (which is an electron transfer enzyme) for estrogen synthesis. The other pituitary peptide, luteinizing hormone (LH), then stimulates the transformation of estrogen-secreting stromal cells in the selected ovary into progesterone-secreting cells, and promotes ovulation. The predominant ovarian hormones, that exert peripheral, central and intraovarian effects, are the sex steroids estrogen or estradiol (E2) and progesterone ($P_4$); there are also other steroids at play in the ovarian and hypothalamic-pituitary events. In addition, there are other peptidic reproductive hormones known as nonsteroidal ovarian factors (e.g. inhibin, oocyte maturation inhibitor, gonadotropin surge-inhibiting factor and certain growth factors).

The properly orchestrated actions of all these substances are known to be necessary for the functioning of the menstrual cycle. The endometrium and the cervix uteri are very sensitive detectors of the hormonal signals and of their orchestration (i.e., of their relative timing with respect to each other) [B. M. Sanborn et al., J. St. Biochem. 9:951, 1978; G. I. Gorodeski et al., J. din. Endocrinol. Metab. 70:1624, 1990; G. Fried et al., Human Reprod. 5:870, 1990; G. I. Gordeski et al., Fertil. Steril. 47:108, 1987]. The periodically recurring development of ovarian follicles, in preparation for the periodically recurring ovulation, is called folliculogenesis. The process of folliculogenesis is the essence of ovarian function from the perspective of ovulation-prediction and it involves four basic conditions in which the many follicles, present in the two ovaries, can be found: resting, growing, atretic, or ready to ovulate [A. L. Goodman and G. D. Hodgen, in R. O. Greep, editor: Recent progress in hormone research, Academic Press, 1983]. Most of the follicles remain resting but, at the beginning of every menstrual cycle, a group or cohort of follicles are recruited to grow; only one of these will mature and will normally ovulate, with the rest of the group succumbing to atresia (death).

It is well established that women and other primate females produce a single fertilizable egg approximately every four weeks. The actual duration of this circamensual (or approximately one-month) period is not a constant; rather, it ranges from about three weeks to about five weeks wherein lies the need for and the challenge of reliable monitoring of the menstrual cycle and of reliable anticipation of the brief fertility window. The brevity of the fertile phase (about 5 days) is due to the limited viability or life-time of the ovulated egg (i.e., the egg released from the successfully matured dominant follicle) coupled with the pre-ovulation fertile days that are due to the life-time of the sperm which survive longer than the ovulated egg but only in the now-hospitable environment of the cervical mucus and epithelium at around the time of ovulation. Allowing for the longer longevity of the sperm is the most difficult challenge for scientific family planning.

Folliculogenesis is a continuous process with well-defined morphologic and endocrine dynamics or timing of events. The dynamics of this process have been characterized biologically and separated into the intervals or stages of recruitment, selection, dominance and ovulation [G. D. Hodgen, Fertility and Sterility 38:28 1,1983]:

| TIMING OF THE FOUR STAGES OF FOLLICULOGENESIS | | | | |
| --- | --- | --- | --- | --- |
| STAGES IN AN IDEALIZED, STEREOTYPICAL MENSTRUAL CYCLE | RECRUITMENT | SELECTION | DOMINANCE | OVULATION |
| Approximate cycle days | 1 to 5 ± 1 | 6 ± 1 | 8 to 12 | 14 ± 1 |

The interval of recruitment begins at the end of the previous cycle, from the onset of menstrual bleeding to approximately day 5 7 of the current cycle. During this interval, LH induces an "angiogenesis" factor from the theca cells, increasing the blood supply and estrogen synthesis by the recruited follicles.

The term "selection" indicates the reduction of the recruited group of follicles down to the species-characteristic ovulatory quota which in women and related primates is one. Selection is the culmination of recruitment on day 6±1. Typically only one of the two ovaries sponsors recruitment and selection of the single dominant follicle which is destined for ovulation. (Spontaneous multiple ovulation is atypical, although not a rarity. It is expected that multiple ovulation should be recognizable with the probe of this invention.)

Dominance is the interval of follicular growth that precedes ovulation after selection and is achieved typically between days 8 and 12 of the stereotypical menstrual cycle. It appears that the one follicle that most rapidly acquires aromatase activity and LH receptors probably is the one that becomes dominant, overcoming an ovarian inhibitory activity that suppresses the less-developed follicles of the recruited group, in the midfollicular phase. The increasing quantities of estrogen are secreted by the dominant follicle and play a critical role in coordinating the development of the different parts of the reproductive tract: estrogen priming is essential in the brain as well as in the cervical epithelium and mucus (where the probe detects its effect) and in the oviduct. The dominant follicle has a straightforward prerogative: it must synchronize the entire reproductive system for ovulation, fertilization and implantation. Failing that, conception will not be possible (such as in the case of the luteal phase defect). This is the essence of the "pelvic clock" or "zeitgeber", the ovarian circamensual pacemaker. However, the mechanism is made more complex by the participation of other pacemakers, including at least one in the brain, in the reproductive cycle (vide infra).

Once the dominant follicle has achieved the necessary size and adequate systemic hormonal effects, final maturational changes within the follicle stimulate ovulation. Endocrinologically, the most prominent marker of impending ovulation is the LH surge which anticipates ovulation within 9 to 12 hours and which is under the control of the ovarian pacemaker that dictates the timing of these events. At the time of the LH surge, the granulosa cells surrounding the follicle become transformed or "luteinized". They become specialized toward synthesis and secretion of progesterone and this rapid increase in progesterone levels is responsible for inducing and coordinating several physiological changes in the reproductive system; the ovulation marker dip or minimum of my prior art fertility probe detects one of them, due to the sensitivity of the epithelium and mucus in the posterior fornix region to the sex steroids.

2.3 The Kirsner Prior Art and the Present Invention

The present invention provides an improvement applicable to any other monitor of the folliculogenesis process that has a similar capability to provide a cyclic profile with this high information content in one variable. Based on the repeatability of the characteristic profile features from cycle to cycle, the data makes it possible to interpret the probe cyclic profile so as to recognize the various phases of folliculogenesis and, in so doing, to distinguish the brief fertility window from infertility and thus anticipate ovulation in a rational manner.

FIG. 10 depicts the features of a menstrual cyclic profile that was yielded by a woman answering the idealized, stereotypical or baseline characteristics. The length of the cycle and its apparent dynamics (or timing of the various intervals or stages involved in folliculogenesis) are chosen to correspond to the stereotypical case of 28 day-long menstrual cycle. The first minimum, FM, occurs in this cycle on day 6 and reflects the selection stage that is the culmination of recruitment. We are justified to view the depicted data on day 6 as FM even m the absence in this particular profile of the prior data points that were not obtained on account of hygienic considerations during the previous days of menstrual bleeding; many other cyclic profiles have consistently shown this first minimum, as illustrated in FIGS. 11 and 12.

FIG. 10 further depicts the wide and high first peak FP that describes the interval of dominance. This is then followed by the window of fertility WF which is defined by boundaries BF (begin fertility) and EF (end fertility) with three labeled features flanked by the boundary points, all within the window WF. These five days define the fertile period during which conception is possible due to the life-times of both the egg and the sperm with the proviso stated below in the discussion of the data interpretation program in relation to the need for large-scale statistical data confirming this definition of WF.

We know from empirical evidence that the third minimum, labeled OM, marks the day of ovulation because in separate experiments it coincided with the day of the LH surge detected in the subject's urine by standard laboratory procedure, radio-immunoassay. (OM also always preceded the rise in BBT when monitored for comparison.) It will be clear to those skilled in the art that ultrasonic evidence of follicle collapse is a more reliable proof of ovulation, if backed by other data eliminating the possibility of follicle collapse without egg release; however, ensuing pregnancy is the only definitive proof of ovulation in absolute terms. Such proof will be obtained in a planned clinical trial, discussed below. The temporal relationship (one day) between the ovulation marker OM and the second peak SP is consistent with a steroid signal from the selected ovary signaling its readiness to release the egg from the dominant follicle.

The most important feature to point out about FIG. 10 is that, while the two horizontal thresholds FT and OT are constants dependent on the calibration of the probe electronics, the boundary days of the fertility window WF (BF and EF, here days 12 and 16) are variables that change from cycle to cycle. This is documented in Table 1 (Window of fertility boundary days for six menstrual cycles). Table 1 shows cycles with cycle lengths ranging from 24 to 30 days, with the beginning of fertility BF ranging from day 9 to day 13, and end of fertility EF ranging from day 13 to day 17. The Table demonstrates how seriously wrong the assumption of the same timing of events in different cycles would be if the assumption were used for the data interpretation method, as has been the case in the prior art by certain competitors. The Table shows that two cycles of a given cycle length (here 26 days) can have two different beginnings of the fertile window (here day 9 and day 13, respectively). The Table also shows that a given beginning of the fertile window (here day 13) can occur in cycles of different lengths (here cycle lengths from 24 to 30 days).

I now introduce a new discovery that is most important for the construction of the data-interpretation program described and claimed below. Due to the mandatory synchronization of the various pacemakers involved in the natural cycling process of the reproductive system, there appears in the probe cyclic profile a phenomenon that I describe more fully below under the name of "synchronization arrest". In connection with it, I have now discovered that the beginning of fertility, BF, is predicted by the amplitude of the probe signal on the day of the first minimum, FM; this is also depicted in FIG. 10.

TABLE 1

WINDOW OF FERTILITY BOUNDARY DAYS FOR SIX MENSTRUAL CYCLES

| Cycle Number | BF Beginning of Fertile Window | EF End of Fertile Window | Length of the Cycle | OM Ovulation Marker Day | Length of Luteal Phase |
|---|---|---|---|---|---|
| A. BASELINE CYCLES | | | | | |
| PM1 | 12 | 16 | 28 | 15 | 13 |
| PM2 | 13 | 17 | 30 | 16 | 14 |
| PM3 | 9 | 13 | 26 | 12 | 14 |
| Baseline Range | 9-13 | 13-17 | 26-30 | 12-16 | 13-14 |
| B. NON-BASELINE CYCLES | | | | | |
| LK4* | 13 | 18 | 26 | 17 | 9 |
| LK5 | 13 | 17 | 24 | 16 | 8 |
| LK6 | 13 | 17 | 28 | 16 | 12 |
| Non-baseline Range | 13 | 17-18 | 24-28 | 15-16 | 8-12 |
| Overall Range | 9-13 | 13-18 | 24-30 | 12-16 | 8-14 |

*Cycle LK4 is a short cycle, as are cycles PM3 and LK5 (<28 days). However, unlike cycle PM3, cycles LK4 and LK5 are abnormal cycles with short luteal phases (<11 days). Both have abnormally long follicular phases, being short cycles, unlike the baseline cycle PM3 which is short simply because of its short follicular phase (with the normal luteal phase of 14 days). Cycle LK4 is unusual in that there are three, ratherthan just one, decreasingreadings after A the second peak. Cycle LK4, which was recorded by a woman with a history of amenorrhea and of ovarian cysts before her two pregnancies, is considered to be a case of asynchrony between follicle maturation and the pituitary signal to ovulation [A. J. Zeleznik, in E. Y. Adashi and P. K. C Leung, editors: The Ovary, Raven, 1993, pp.41-45; G. F. Erickson in J. Schoemaker andR. Schats, editors: Ovarian Endocrinopathies, Parthenon, 1994, pp. 103-115; E. L. Nestour et at, J. Chin. Endocrinol. Metab. 77: 439, 1993], involving the circhoral clock of the hypothalamic GnRH pulse generator on which the circamensual ovarian clock is "obligatorily dependent" IJ. Hotchkiss and Knobil in E. Y. Adashi, J. A. Rock and Z. Rosenwaks, editors: Reproductive Endocrinology,Surgeiy, and Technology, Lippincott-Raven Publishers, 1996].

The multitude of repeatable measurable features of the probe cyclic pattern makes it possible to determine the boundaries of the fertile window for every individual cycle rather than having to rely on some assumption of unchanged timing of these events from cycle to cycle in the manner of the methods of prior art discussed above. The Kirsner method of electrometric monitoring of the tissues and secretions in the posterior fornix region for the end-organ effects of the endogeneous bioactive substances is a significant improvement upon the use of the hormone concentrations by the prior art competitors such as Unipath Ltd. Reliance on the hormone concentrations to define the fertile period is an inherently unreliable approach because the hormones are merely the input signals into the physiological mechanism of fertility status rather than indicators of the fertility status per se.

Monitoring of the end-organ effects may produce two kinds of deviations from the idealized, stereotypical menstrual cycle. These deviations from stereotype are variously considered to be consequences of the industrial and post-industrial age lifestyle, diet and environmental estrogens or, more generally, pollution. Chemically-speaking, free radicals and abnormal cross-linking of macromolecules in the tissues are often involved. These are electron transfer reactions whose effects are detectable by the Kirsner probe but not by the other prior art techniques including the Unipath Persona. Those techniques cannot therefore detect the deviations from "norm", or stereotype, which is one reason why the concept of the stereotypical menstrual cycle continues to be perpetuated in the literature. The deviations of the first kind are the merely quantitative variations of the idealized menstrual cycle, leading to near-stereotypical cyclic profiles such as those included in FIGS. 11 and 12. The other kind of deviation is more serious, causing qualitative changes diverging from the stereotype, leading to aberrant cyclic profiles associated with reduced fertility and female infertility; this includes, for example, the case of the quite frequently occurring luteal phase defect (FIG. 22). Even some of the near-stereotypical profiles may turn out to reflect more than biological variables, and may be found to represent a syndrome (e.g., the short luteal phase cycles LK4 and LK5, particularly cycle LK4). Adjustments to the programming of the intelligent probe may result from the forthcoming clinical trials. Any such adjustments will be within the scope of this invention.

SUMMARY OF INVENTION

The inventive apparatus and method include:

discovery that probe cycle profile is tied into folliculogenesis, the process of preparation for ovulation how the profile correlates with the individual events or intervals of folliculogenesis (ovarian function)

how this correlation enables fitting data points into the profile which leads to a method that translates the intuitive thinking process of an expert into the logics of a formalized data-interpretation method that reliability of the fit, i.e. of diagnosis, can be quantified method of this quantification and of its display by the instrument factoring into the confidence level descriptor the statistics of conception probability for the day, established in a clinical trial designed around the single-attempt requirement that guarantees homogeneity of the data.

method of fitting data either into extended or into partial context of prior data inventory in the present cycle definition of fertile window, i.e., defined with reference to probe profile features including the instant recognition of BF via its prediction by earlier profile features (FM, g, etc.)

method of using clinical trial data to define the numerical ranges for each of a number of inter-related characteristic features of the cyclic profile as qualifiers for compliance queries in the cross-correlation process of data interpretation (this contrasts with competitors' reliance on a fixed average value of a single feature such as the Unipath Persona's use of the E3G threshold)

miniaturized single piece format of probe user friendly combination of hardware and software features (hardware features in the form of simple buttons and alpha-numeric display in natural language) e.g. allows days set to be entered late; does not interrogate user beyond minimal requirements I-button to register intercourse makes it possible to electronically record intercourse for pregnancy-planning purposes, including 1) calculation of expected date of delivery and 2) fetal sex preselection probability assessment method of data management for optional downloading into an external display appliance method of data management for optional data offloading for memory clearance, in relation to limited capacity of the memory method of enabling continuous use of the intelligent probe despite the memory size limit continuous layout (e.g., rectangular or circular) of the memory makes it possible to avoid full memory preventing continued functioning, by erasing the oldest stored data and preserving, by this design, the most recent stored cyclic profiles day set button for day 1 or +1 or −1 is oval shaped, press and rocker combination (allows also to set day belatedly or to change the setting)

download initiation control is turn-screw on back, independent of daily use (to conserve energy and to simplify use)

Web TV download capability and capability to download on ordinary TV with a decoder-interface unit capability to recognize an abnormal cyclic pattern as either a non-classical profile of a fertile cycle or as an aberrant profile of an infertile cycle (present method applies to classical profiles and, through the "complies?" query in the second decision routine, to non-classical profiles by extension)

complementary or alternative method of data interpretation, called the method of normalized or, generally, transformed data

DETAILED DESCRIPTION OF THE PREFERRED EMBODIMENTS

The present invention is directed to electronic interpretation of data, monitored in relation to the day of cycle, on the physiological state of the cervix uteri and cervical mucus by means of the probe of my prior art patent application, and to automatically providing a display of the current fertility status. This is based on the measurement with the probe depicted in FIGS. 1 to 5. The electronics of the probe contain a microchip, preferably an application-specific integrated circuit with a microprocessor, that performs the measurement as well as the data interpretation and data management according to the methods and programs of the present invention.

Figure 1:
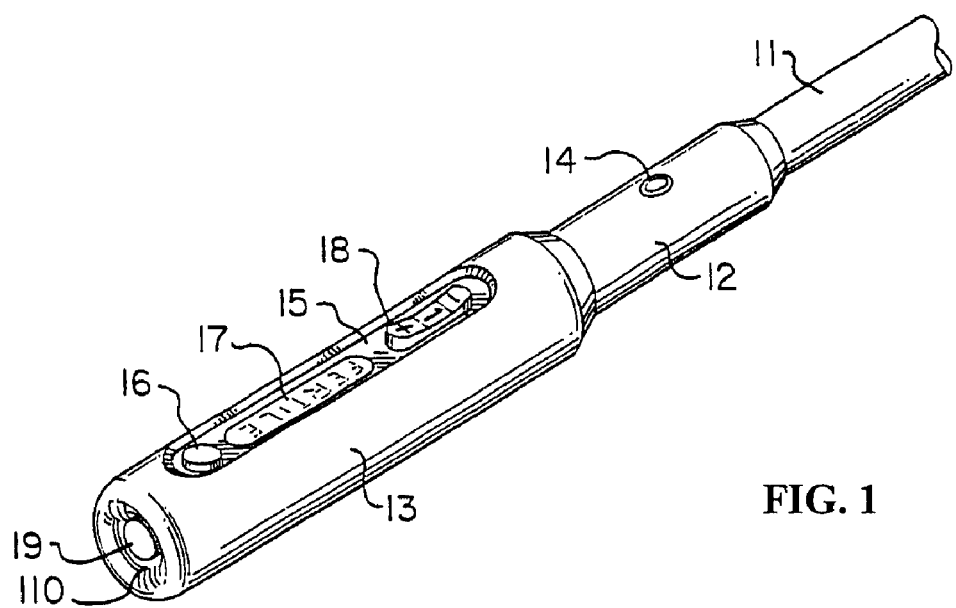
FIG. 1 is a partial perspective view of a preferred embodiment of the intelligent fertility monitor of the invention, showing the arrangement of user-interface features appearing, in this embodiment of the apparatus, at the front or top side and at the bottom.
Figure 2:
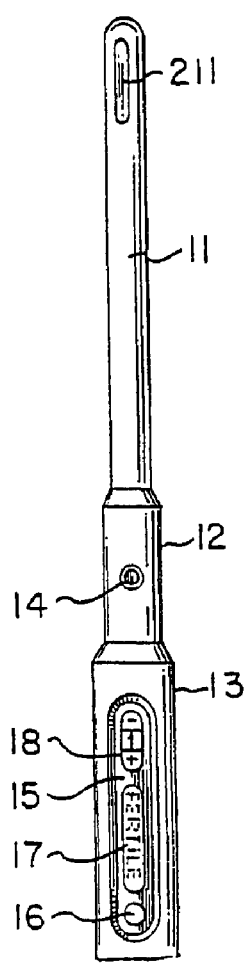
FIG. 2 is full front view thereof depicting the user-interface and other features on the front or top side of the apparatus.
Figure 3:
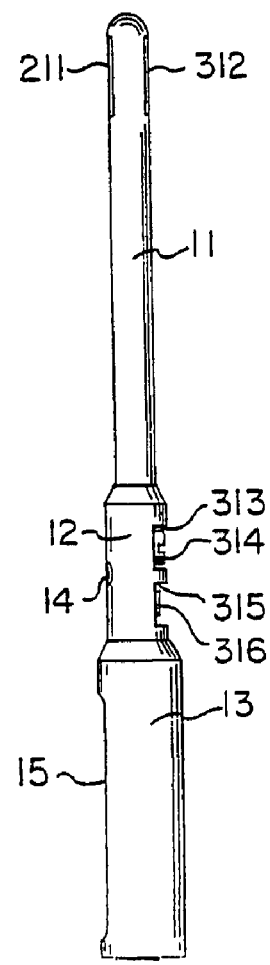
FIG. 3 is the right side view thereof depicting the controls on the back viewed from the side.

FIGS. 1 to 4 are perspective, front, side, and rear views of the intelligent probe. FIGS. 1 to 4 resemble a fertility probe of my prior art, in particular they resemble the mammalian fertility probe of my design patent application filed under docket number 9064/102 to which I am now adding new features that provide for the intelligent characteristics of the apparatus of this invention. The probe comprises several cylindrical sections, preferably three as shown. The first section is a rigid or semirigid cylindrical body 11 approximately 10 centimeters long and 1 centimeter in diameter. The first section 11 has a rounded distal or insertion end insertable into the vagina, with the insertion end extending into the region of the posterior fornix with electrode 211 of FIG. 2 contacting the cervix. Two electrodes or elements 211 and 312 in FIG. 3 are embedded into probe body 11. The electrodes 211 and 312 can be of any shape and size within reason. The attachment of the electrodes to the body can be accomplished by any method known for attaching an electrode to a substrate, including, but not limited to gluing, bonding and embedding. The cylindrical body 11 of the first section may be modified in any of the ways anticipated by my patent application "Method and apparatus for monitoring fertility status in the mammalian vagina" filed under docket number 9064/101.

Figure 4:
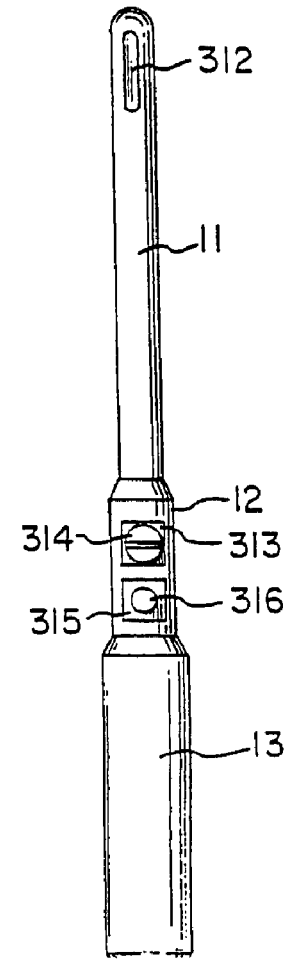
FIG. 4 is a rear view thereof depicting the controls on the back as seen from the rear.

The second section 12 may be of a larger diameter but smaller than the third section, as shown, but this mid-size diameter is a cosmetic rather than a functional feature. The second section contains three functional elements, one on the top or front side and two on the back. An infra red or other data transfer interface port 14 appears as a small opening on the front side defined as the side that carries the display-cum-controls well 15 and the electrode 211. On the back side of this section are, as seen in FIGS. 3 and 4, two wells 313 and 315 with two buttons 314 and 316 that are provided to control the less frequently used functions. The screw-like button 314 initiates, by being turned 90 degrees, data downloading once the port 14 is lined up with the corresponding port on a data receiving device. This function is independent of and separate from the daily-use program, in order to conserve energy and, equally significant, to keep the operation user-friendly (undemanding). The well-recessed small button 316 is used to register intercourse and save its timing (day of cycle) in the memory of the intelligent probe. Either or both controls 314 and 316 may be behind a little door (or two separate doors) protecting them further from accidental actuation. Other possible embodiments of the I-register input control include a sliding switch that slides from one groove into another and back, or two buttons that may be concentric and must be pressed together.

The port may be located in the third section instead of in the indicated position, interchanging the location with the "confirm" button 19, in another embodiment of the apparatus of this invention. It could also be located closer to the well 15, either on the second section 12 or on the third section 13.

The third section 13 carries most of the microelectronics and is the handle of the hand-held probe device. The oblong narrow well 15 carries the ON button 16 at the proximal end, followed by the LCD (or LED or other) display 17. This is then followed by the special control 18 which is a rocker switch that enables either positive (+) or negative (−) response to a displayed question, or adding 1 to (+) or subtracting 1 from (−) a displayed numerical value. The control switch 18 also makes it possible to perform its key role, which is the initialization of the day of cycle counter (or relative time clock), by being pressed straight down in its flat middle portion, where the numeral 1 is seen embossed or otherwise imprinted on its surface. Other possible embodiments of the control element 18 include three separate buttons or other switches performing the same roles. They could be located outside of the well 15 such as on the opposite, back, side of the third section 13.

At the proximal or non-insertion end of the intelligent probe is the "confirm" button 19 located in a crater-like well 10 the purpose of which is to prevent accidental actuation of the control 19. In another embodiment of the intelligent probe, the "confirm" button 19 and the well 110 are not present because the role of the "confirm" button is performed by the plus (+) segment of the controls 18 (or by a separate button as noted above in discussing other possible embodiments of the control button 18. The space in which the "confirm" button 19 is now shown in FIG. 1 may be utilized for an external power supply connection useful for data downloading (and/or offloading) under the control of the intelligent probe. This preserves battery life for the daily use of the intelligent probe.

Figure 5:
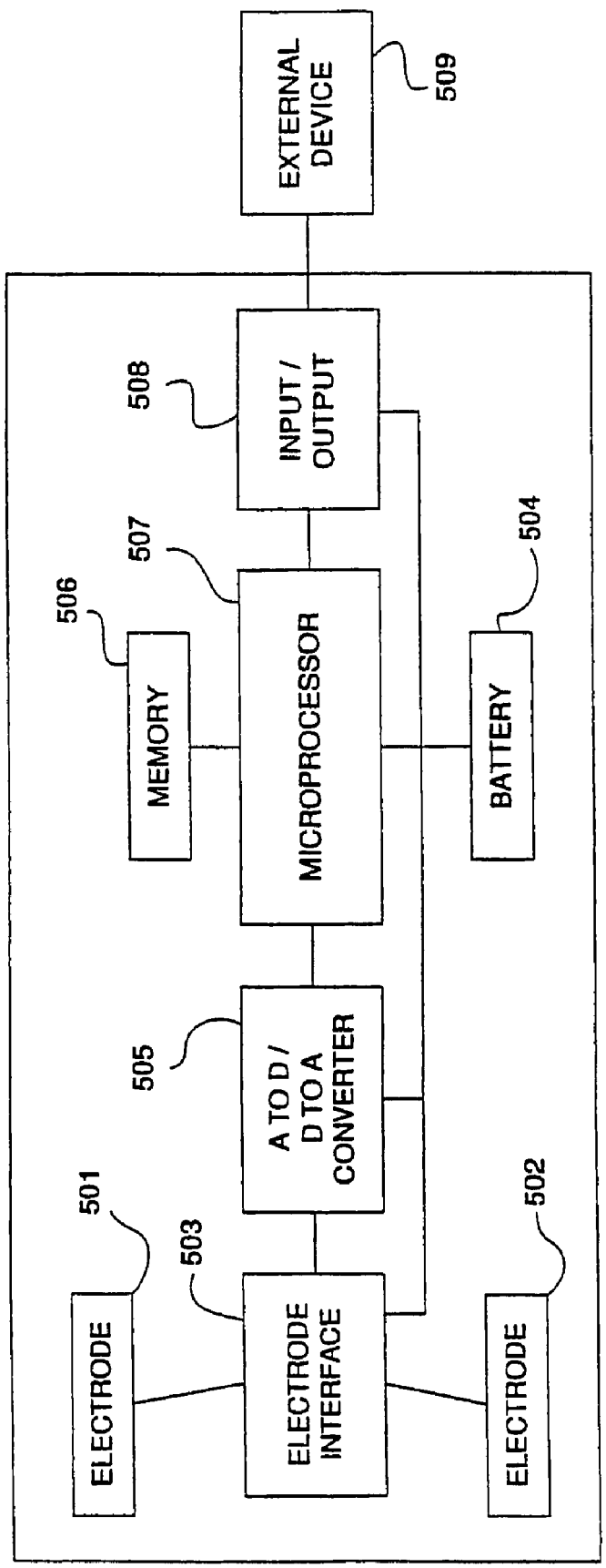
FIG. 5 is a block diagram of the electronics of the intelligent probe depicted in FIGS. 1 to 4.

FIG. 5 is a block diagram of the electronic configuration of the probe of the invention which involves a microchip, preferably an application-specific integrated circuit. The electrodes 501 and 502 are actuated by means of the electrode interface conditioning electronics 503 by a waveform digitally generated by the microprocessor 507. The waveform is applied after conversion into an analog signal in the A to D/D to A converter 505 which then also converts the electrode response to digital data for processing by the microprocessor 507. Unlike in the previous generation of the fertility probe, data processing now includes the data-interpretation treatment which is the subject of this application. The processed data is displayed on LCD (or LED or other) display and stored in memory 506 for use as context for data interpretation on following days of the present menstrual cycle; the stored data can also be optionally downloaded later (for display and analysis) via the input/output interface 508 into an external device 509.

The external device is typically a personal computer which may be dedicated to this purpose of analyzing patient data in a physician's office. It may also be a decoder-interface unit custom-made for the purpose of receiving the data from the probe for display on an ordinary television set or on the new generation of computer-TV hybrids (such as the Web-TV, for example). A Web-TV may be equipped with an infrared port and may thus be able to receive the data directly, without the decoder-interface device. For such a case in particular, the intelligent probe includes an embedded program for elementary manipulation of the TV-downloaded multiple cyclic profiles, for the user's convenience. In this way, the intelligent probe may provide access to the new generation of the so-called natural family planning to almost any woman in any household, regardless of whether they do or don't own a home computer. This is useful since TV set ownership is generally more widely spread than personal or home computer ownership.

Figure 6:
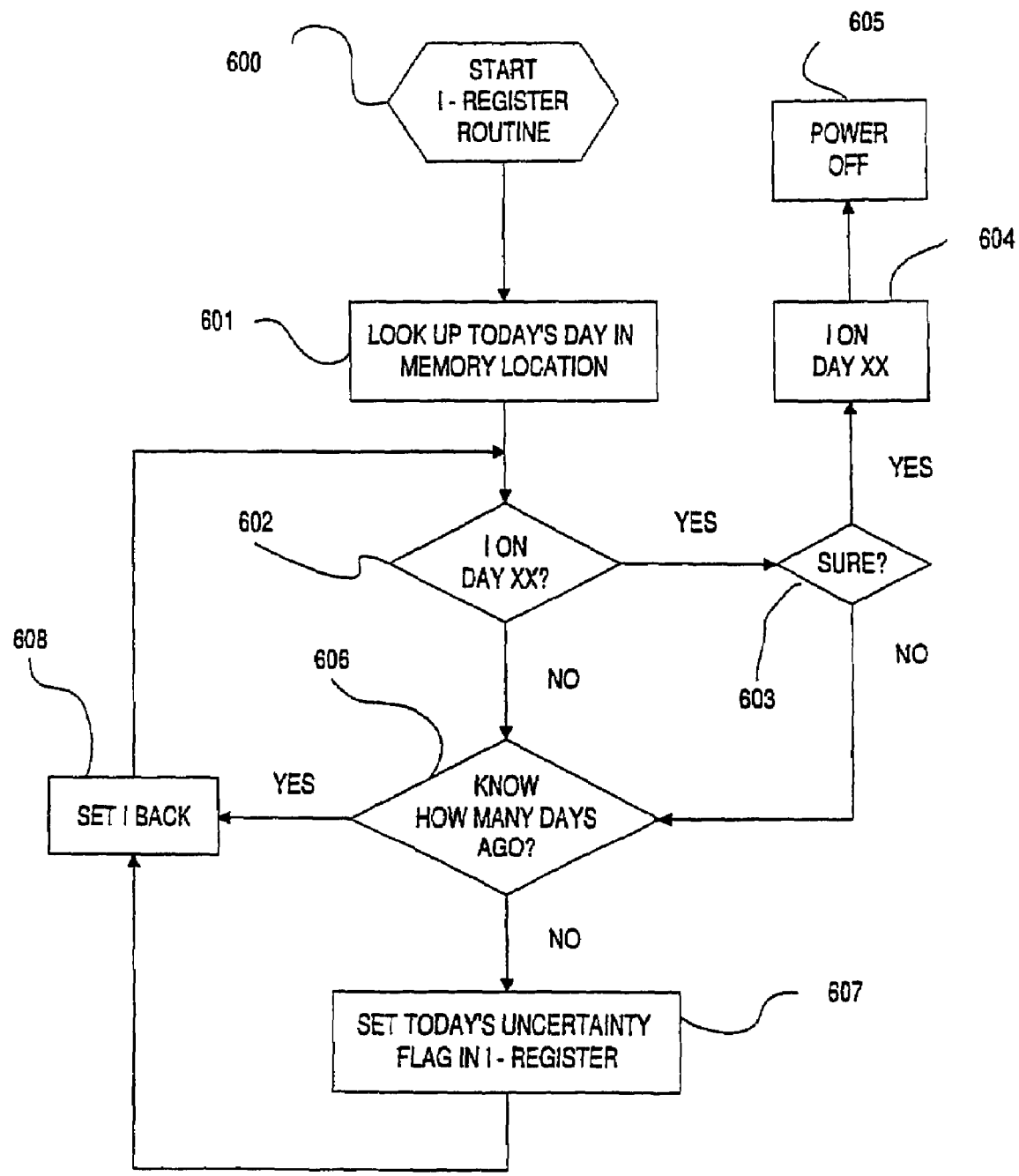
FIG. 6 is a flow diagram of the program associated with the actuation of the intercourse-register I-button 316 in FIG. 3.

FIG. 6 is a flow diagram of the program associated with the use of the intercourse-register I-button 316. This routine is independent of the data-interpretation program and of the daily-measurement procedure; it is initiated by pressing the I-button 316 and terminated automatically by switching power off once the entry into the I-register is completed. The routine allows for a belated retrospective entry and for a possibly uncertain timing of such a retrospective entry. In the event the woman-user forgets to register the intercourse on the day, and then later wants to do this retrospectively but is not certain of the time elapsed, the routine downgrades reliability of the I-register.

Under the preferred normal circumstances, the user activates the I-registering routine on the day of the intercourse. The function of the I-button 316 commences with START I-REGISTER ROUTINE block 600 and proceeds to look up in today's memory location the day of cycle XX (and/or date) in block 601. This is then queried in block 602. In response, the LCD 17 displays the entry "I on day XX?" as a question with a flashing question-mark, prompting the woman to confirm this in inquiry block 603 (XX represents here today's day of cycle, e.g., 09 or 15, as the case may be) by pressing the "confirm" button 19. Upon this confirmation, the question-mark is extinguished as an acknowledgment of the confirmation and the entry is made in the I-register as in block 604, and the power is turned off in Block 605. Repeated entries on the same day simply write over without further changing the I-register status, i.e., intercourse on a given day is registered whether it occurred and was entered once or more than once.

If the woman is making the registration on a following day, today's day of cycle XX is not confirmed in inquiry 602 by pressing the minus sign on button 18, and consequently the inquiry KNOW HOW MANY DAYS AGO? is made in block 606. In response she either steps the I-register down using button 18 by one day or by whatever number of days she remembers as the elapsed time with confidence, or she registers her uncertainty first by setting the flag in block 607, before setting the I-register back in block 608 by the guessed number of days using again button 18. The uncertainty will eventually be displayed on the downloaded cyclic pattern graph as "I?" instead of the definitive "I". Either the definitive "I" or the uncertain "I?" will appear on the time (day of cycle) axis of the graph and also by or in place of the respective data points in the line graph displayed on the external device 509. The realtime, calendar date, will also be displayed. The calendar date information is useful for the purpose of calculating the estimated date of delivery, in case of conception resulting from the intercourse. The day of cycle information may be used for the purpose of fetal sex preselection.

Figure 7:
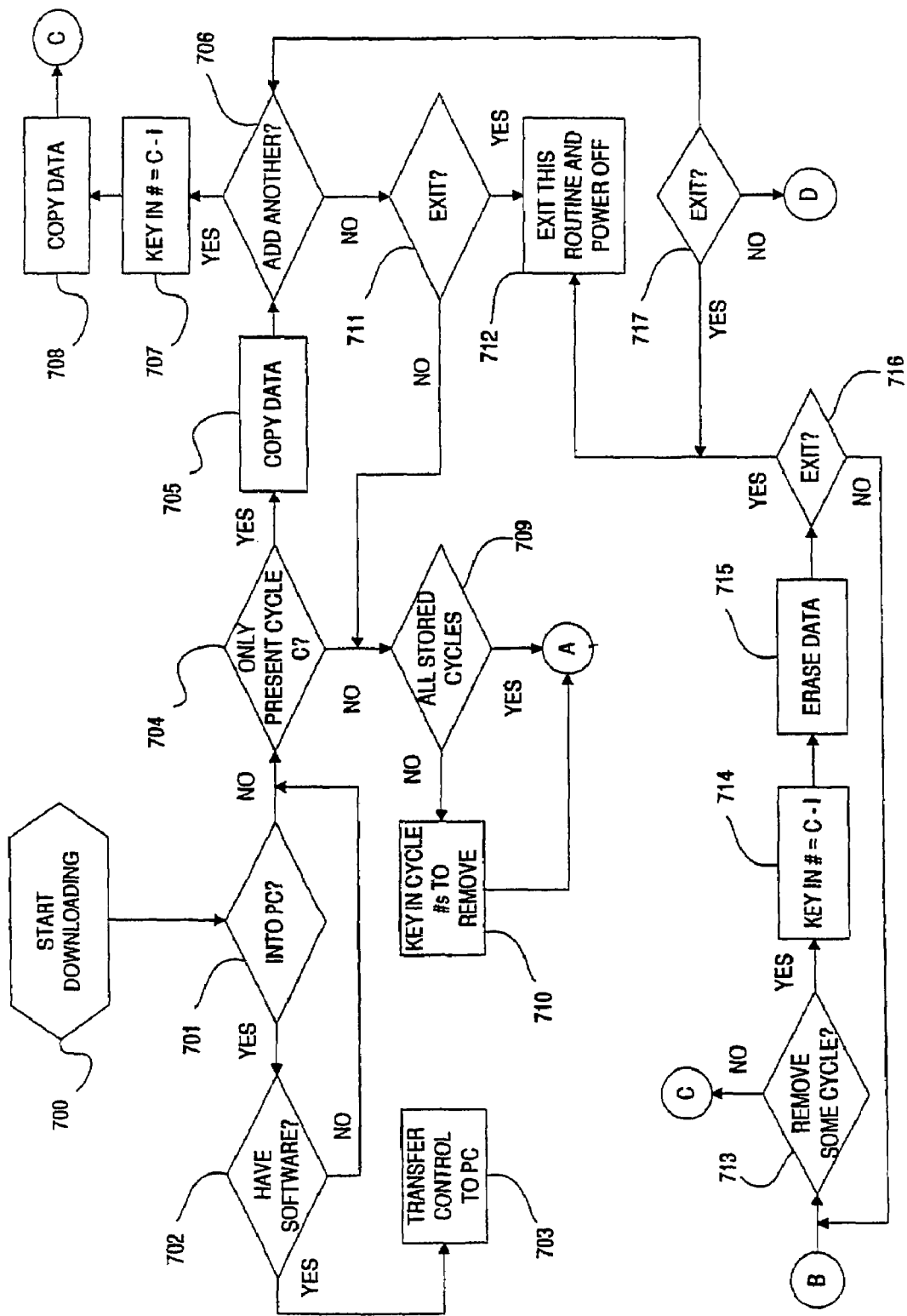
FIG. 7 is a flow diagram of the program associated with the actuation of the download control 314 in FIG. 3 that initiates the downloading into an external display appliance for viewing.

A similar design approach is adopted for the control of the optional data downloading into a display appliance (external device 509), whether it be a personal computer or a Web TV or the proprietary decoder-interface unit for interfacing with an ordinary TV set. The guiding principle is again to achieve user-friendly simplicity and power-supply energy conservation. FIG. 7 is a flow diagram of the program associated with the use of the download control 314. The program, which commences with START DOWNLOADING block 700, first enables to decide, through the inquiry of block 701, whether to download data via blocks 702 (HAVE SOFTWARE?) and 703 (TRANSFER CONTROL TO PC) into a personal computer which then can take control over the downloading process; or whether the downloading will be into another display appliance that is devoid of the required software. In the latter case, a simple data manipulation is made possible by the intelligent probe using the few already described elements of the user interface, contained within the third section 13 of the apparatus.

FIG. 7 describes the process of downloading, i.e., data-copying, under the control of the intelligent probe. Any amount of data may be downloaded for display on the external device 509, whether only the present cycle or all stored cycles or anything between these two extremes. However, only the total of the raw data can be offloaded so as to make the probe's memory all available again for new data. The user is not allowed to edit the data for offloading while she can manipulate the data for viewing on the external display appliance 509, the simple display manipulation sub-routine being described in FIG. 9 (shifting data along the day of cycle axis). Care is taken to allow offloading, for external archive storage, only of the complete set of raw data, unaffected by the manipulation available in the display sub-routine (particularly the option to erase or display only some of the stored cyclic profiles).

Once the decision has been made in block 701 to download under the control of the intelligent probe, the inquiry is made in block 704 whether only present cycle data is to be downloaded. If so, copying of data proceeds as per block 705 (using the confirm button 19). With that cycle displayed on the display appliance, additional cyclic profiles may be added to the display via blocks 706 (ADD ANOTHER?), 707 (KEY IN NUMBER=C−i) where C is the present cycle number and i is an integer for counting cycles backward, and finally block 708 (COPY DATA). Negative response to the inquiry in block 704 allows to download all stored cycles (via block 709) or almost all after selective deletion in block 710. Either option goes to the sub-routine of FIG. 8. Negative response to the inquiry in block 706, namely no more stored cycles to be displayed, proceeds to exit in block 712 via the inquiry 711 which allows for a change of mind on the part of the user who may, upon viewing the present cycle data, decide to view all stored cycles rather than adding some of them piecemeal as already described.

Figure 8:
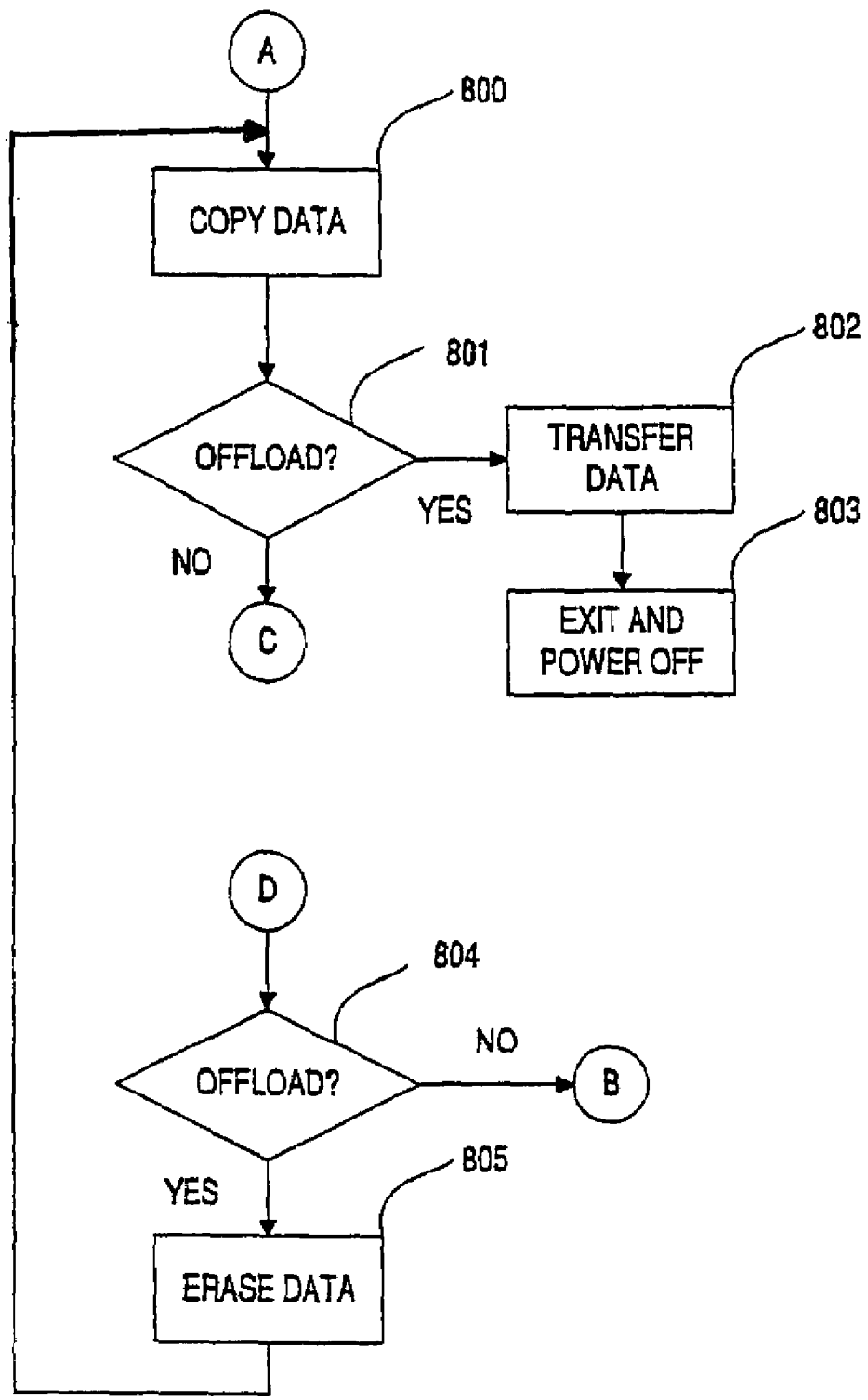
FIG. 8 is a flow diagram of the routine, within the downloading program of FIG. 7, that either offloads the complete contents of the intelligent probe memory for the purpose of memory clearance or, alternatively, erases some of the downloaded cycles from the display on the external display appliance.
Figure 9:
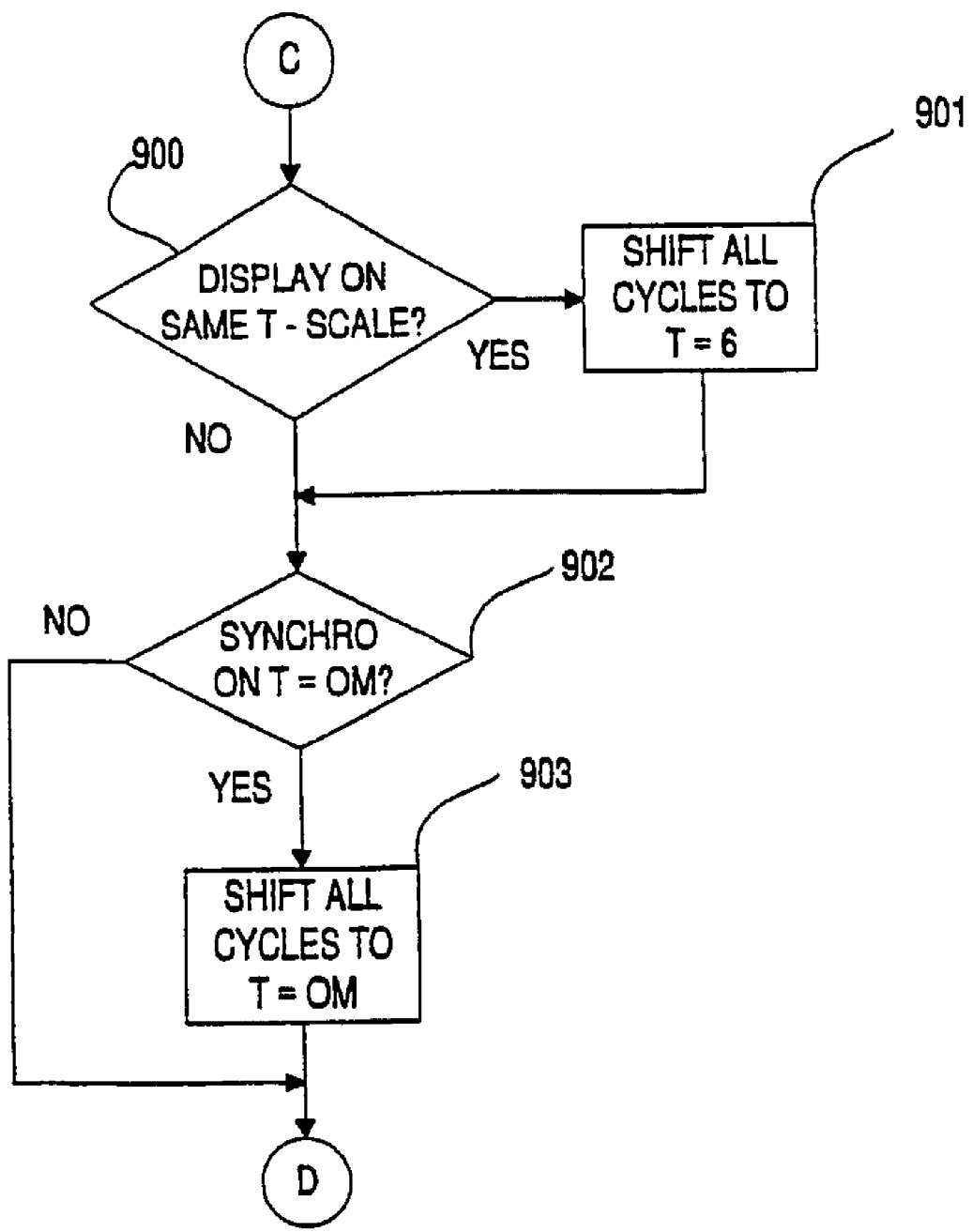
FIG. 9 is a flow diagram of the simple data manipulation routine within the downloading program of FIG. 7, that performs shifting of the probe data along the time (day of cycle) axis.

The remainder of the logical elements in FIG. 7 describe the functions performed upon return from the two sub-routines shown in FIGS. 8 and 9. The inquiry in block 713 allows the user to remove some cycles from the display on the external appliance upon return from the "offload or merely view" sub-routine of FIG. 8. This is achieved by means of blocks 714 (identifying the cycles to remove, 715 erasing) and 716 (deciding to whether to exit or whether to remove some more data for a simplified viewing display prior to eventual exit via block 712). The inquiry of block 717 handles the return from the "simple display manipulation" sub-routine of FIG. 9. The feature to note in FIG. 7 is that the woman can first examine the data selectively, before returning to offload the total memory contents in its raw state.

FIG. 8 is a flow chart of the sub-routine that offloads the entire memory contents of raw data. After block 800 has copied the data, the inquiry is made in block 801 whether to offload or not. The user responds via the plus or minus control 18, possibly in combination with the confirm button 19. If affirmative, the entire memory is transferred in block 802 into the external appliance capable of receiving the data (e.g., a personal computer), the sub-routine is exited and the intelligent probe is powered off (in block 803). If the user does not wish (or cannot) offload, the program goes into the sub-routine of FIG. 9 via the connector C. Also included in FIG. 8 is a return from the sub-routine of FIG. 9 via the connector D. This allows the user to change her mind, in block 804, and offload the previously viewed and manipulated data but only after the data set has been returned to its raw state: to that end, the displayed data is erased in block 805, then the entire memory is copied again in block 800 and offloaded via blocks 801 and 802 as already described.

FIG. 9 performs the rudimentary data manipulation that is of significance to any woman interested enough in the history of her menstrual cycle data to wish to review it on a display screen. The "raw state" of the consecutive cycles is a sequence showing the several months worth of menstrual cycles one after another so that the last day of cycle i is also the first day of cycle i+1 as per the well known convention. The sub-routine first enables a decision in block 900 (by means of the plus or minus functions of the control 18, possibly in combination with the confirm button 19) whether to display the data on the same time scale, i.e., in the manner of FIG. 11 or FIG. 12. If so, all the data are shifted accordingly. After a time delay, the next inquiry is in block 902, namely, does the user want to synchronize the displayed cyclic profiles on the day of the ovulation marker (SYNCHRO ON t=OM?). This inquiry would also be arrived at had the previous type of display not been desired by the user. The shift is performed by block 903 and, after a time delay, the sub-routine connects with the offloading sub-routine via connector D, as already discussed in FIG. 8 above.

A very important feature of the design is the option, open to the woman-user, to continue using the probe without offloading (i.e. without clearing up) a full memory. This is achieved by retaining the most recent preceding cycles in the inventory and erasing the most distant, the oldest stored data; she therefore always has the most recent history (whether it be six or twelve cycles or whatever the limit capacity built into the apparatus) available for examination. This is made possible by the continuous layout of the memory discussed below in connection with the bookkeeping routine for stored prior cycles.

The main control button 16 initiates, by switching on the power, the daily measurement and its diagnostic interpretation. The data-interpretation program interprets today's probe measurement data: it develops the diagnostic meaning of the data in terms of fertility status (either fertile or infertile). It does that by cross-correlating the amplitude of the probe signal with at least one other running variable, day of cycle, as measured by the instrument's clock which must be set to day 1 on first day of menstruation. (Other measurement variables may be introduced to potentially increase the quality of interpretation at the cost of increased complexity of the program and of increased production cost of the probe.)

"Cross-correlation" means to answer the question: What probe data interpretation is consistent with the other running variable, namely the day of cycle? The method used in this application is based on fitting data points into a curve that has a multitude of reproducible features. Other methods, known to those skilled in the art (such as artificial intelligence methods) are to be considered as falling within the scope of this invention.

The data-interpretation program is based on the reproducibility of the features of the probe cyclic pattern (or "profiles"). The characteristic features of the profiles were described in section 2.3 with reference to FIG. 10 and further experimental evidence is illustrated by three baseline and three non-baseline patterns in FIGS. 11 and 12. The three baseline cyclic profiles in FIG. 11 were obtained with three probe monitors PM1, PM2, and PM3 by three clinical trial volunteers who satisfied the criteria for baseline characteristics. They were perfectly healthy young women below the age of 35 (here 26 to 30 years of age) who used no medication and no contraception. They had no prior pregnancies and they were non-smokers. The term "baseline" refers to the fact that these women were characterized by minimal, if any, potential complications of physiological or biochemical nature that could cause deviations from a norm or baseline; they were as close to the idealized, stereotypical menstruating female as can be.

Figure 10:
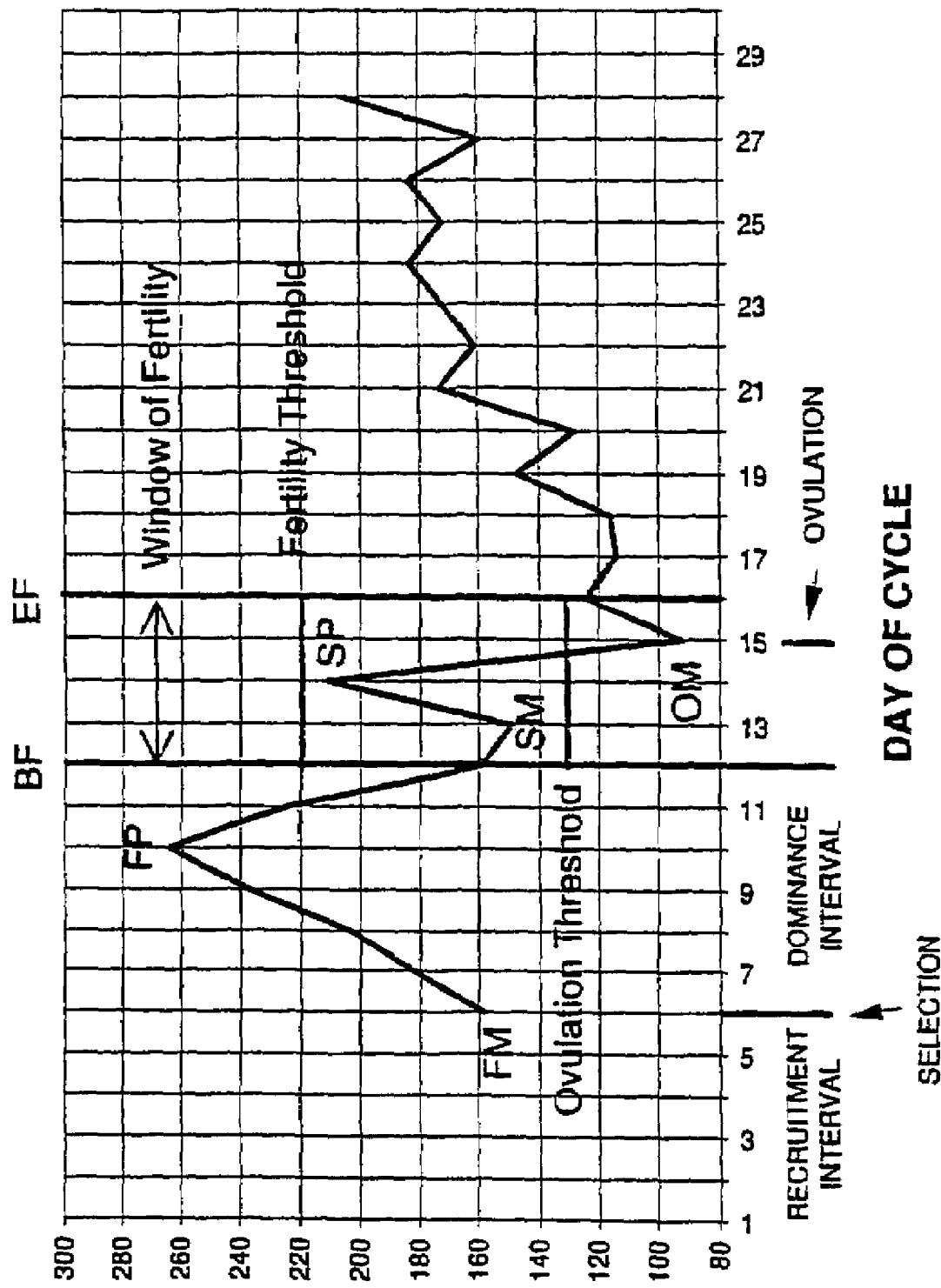
FIG. 10 depicts the probe cyclic profile that corresponds to a stereotypical menstrual cycle of 28 days duration and is labeled with the features of the profile so as to establish the terminology for the data-interpretation program of the present application.
Figure 11:
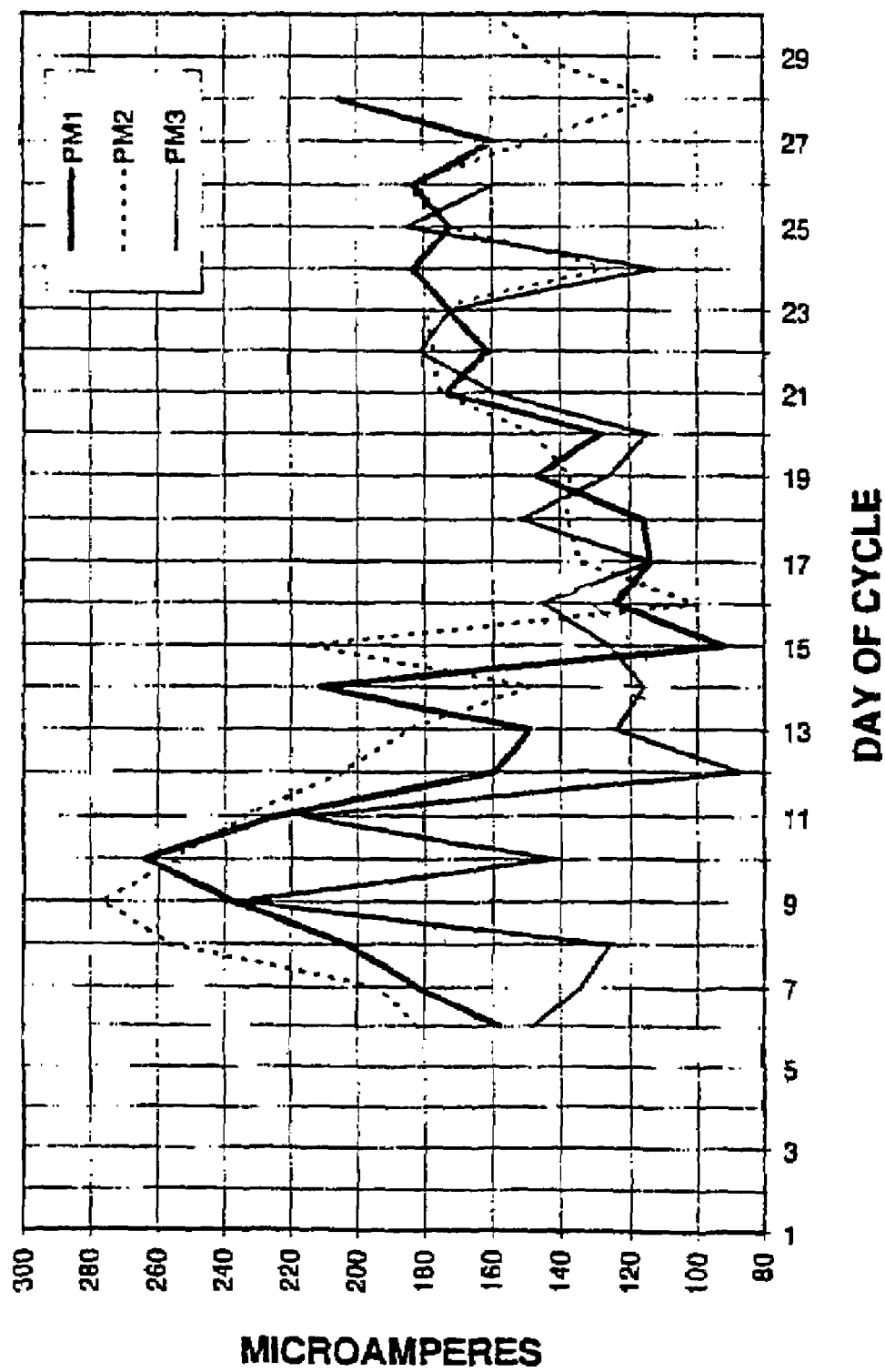
FIG. 11 shows three baseline cyclic profiles discussed in the application.

The baseline cycles in FIG. 11 exhibit at least two important characteristic features that were not known at the time of filing my U.S. '247 patent and the subsequent patent applications. One, the data of the first minimum, FM, predicts the amplitude of the probe signal on the day of the beginning of the fertile window, BF, which is the end of the interval of dominance (refer to FIG. 10). And two, the end of the dominance interval is followed by a slowdown in the descent of the probe signal from the first peak, FP (into the second minimum, SM) which anticipates the ascent forming the second peak. I refer to this slowdown as a "synchronization arrest". I consider both these characteristics a consequence of the ovarian mechanism that regulates the antral fluid steroid milieu, i.e., an indicator of the intrafollicular hormonal profile of the dominant follicle [E. Y. Adashi, J. A. Rock, and Z. Rosenwaks, editors: Reproductive Endocrinology, Surgery, and Technology, Lippincott-Raven Publishers, 19961.

Those skilled in the art of reproductive physiology or endocrinology will appreciate the significance of these phenomena, tied to the previously mentioned (section 2.2) prerogative of the dominant follicle to synchronize the entire reproductive system in order to make conception possible. The "synchronization arrest" is significant also with respect to the short luteal phase phenomenon as illustrated by two of the non-baseline cycles in FIG. 12 (cycles LK4 and LK5). I believe that the mechanism involved in some maimer the brain, probably the circhoral clock (the hypothalamic GnRH pulse generator) on which the circamensual ovarian clock is obligatorily dependent; or this could be a case of failed gonadotropic (LH) support by the brain for the corpus luteum's pre-programmed luteolytic self-destruct mechanism. It is significant that the details of the luteolytic control mechanism in primates are yet to be worked out [ibid. idem.]. The complexity of the measurements of the differences between intrafollicular and circulating levels of hormones adds to the significance of the two probe profile characteristic which reflect what is going on in the ovary.

Figure 12:
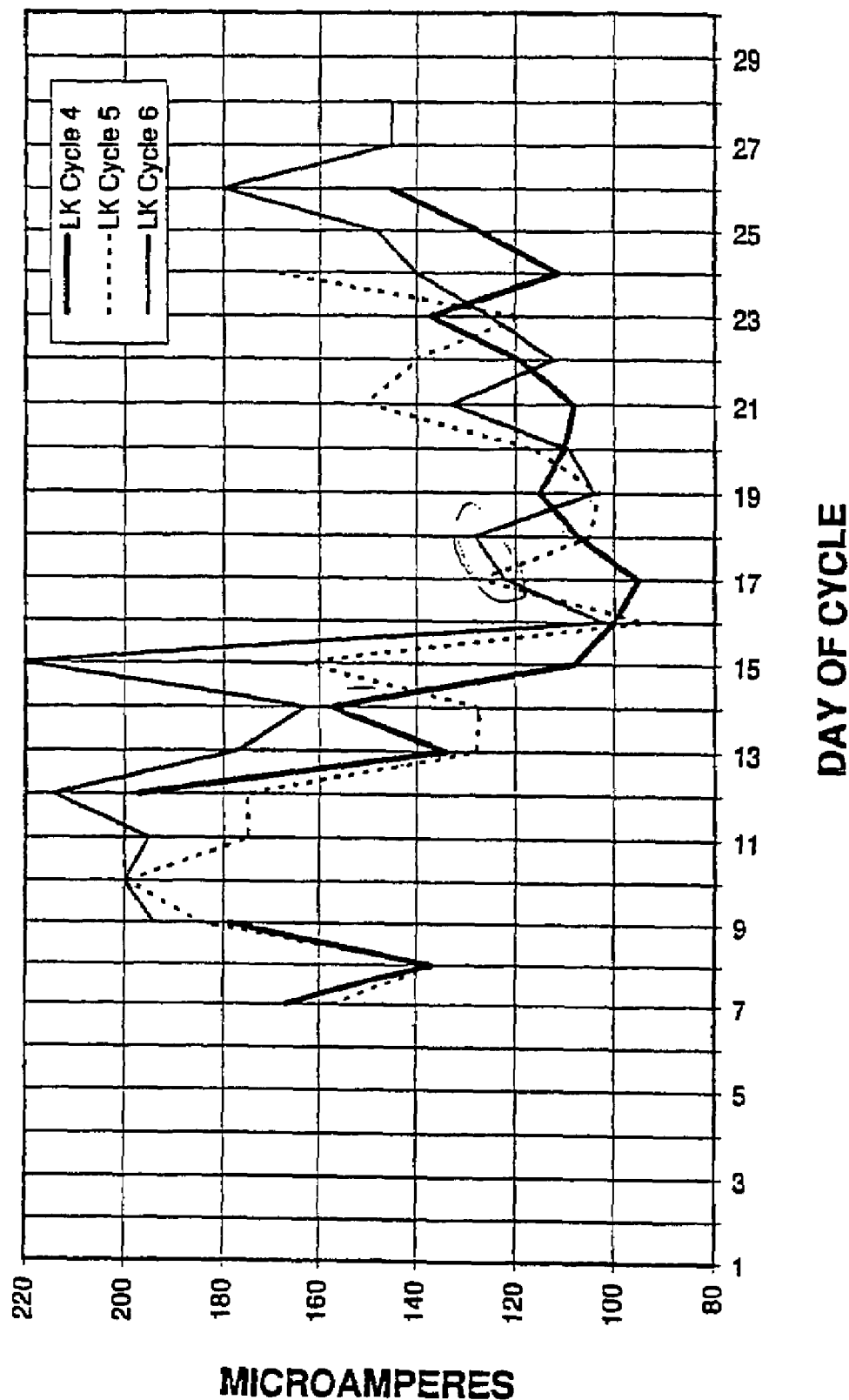
FIG. 12 shows three non-baseline cyclic profiles discussed in the application.

The three non-baseline cyclic profiles in FIG. 12 are three consecutive menstrual cycle probe records by a subject who did not satisfy the baseline criteria. Mrs. LK was not "chemically clean" because she was a cigarette smoker; she also routinely ingested various nutritional supplements that may have affected her reproductive biochemistry and physiology. She was over the age limit of 35 and had some history of amenorrhea, and of ovarian cysts diagnosed years earlier by palpation. She was also a mother, unlike the baseline subjects. In the years before her pregnancies, her cycles were consistently rather long, at 34 or 35 days (as opposed to her cycle lengths here of 24, 26, and 28 days). The non-baseline cyclic profiles in FIG. 12 nevertheless exhibit the same features as those in FIG. 11 that were obtained under more controlled laboratory conditions.

The non-baseline profiles do present certain quantitative deviations from baseline: namely, in two cases (cycles LK5 and LK6) their dynamic range is significantly lower compared to the baseline cycles in FIG. 11, and their post-ovulation (luteal) phase is not of the normal, inherent, length of 14 days (12 to 16). In such cycles with short luteal phases (<11 days), observed more often in older women, there is a lack of synchrony between the ovarian and the menstrual events due to a luteal-phase mismatch between the ovarian steroids and the pituitary peptides (S. K. Smith et al., J. Reprod. Fert. 75:363, 19851. Mrs. LK's history of amenorrhea and ovarian cysts is pertinent to the case of short luteal phase. However, so is stress and its effect on the GnRH hormone generator in the hypothalamus of the brain, that affects the output of the pituitary peptides. For example, it is known in a general way that norepinephrine and possibly epinephrine in the hypothalamus increase the GnRH pulse frequency. Conversely, the endogeneous opioid peptides, the enkephalins and beta-endorphin, reduce the frequency of the GnRH pulses. These interactions are particularly important at the time of the midcycle LH surge, affecting its timing and intensity [W. F. Ganong, Review of Medical Physiology, 17th edition, Appleton & Lange, 1995, Chapter 23]. The slow rate of descent of the data from SP to OM is a useful diagnostic variable that differentiates cycle LK4 from cycle LK5. It is indicative of an extended period of time required in cycle LK4 for the two "clocks" (the circhoral and the circamensual) to become synchronized as a precondition of ovulation. Further, these "real life" (non-laboratory) records also contain gaps in data and possible effects of improper sensor positioning, in addition to the deviations from "ideality" (or stereotype). They therefore present a "real life" test for the data-interpretation program.

The program does not analyze the data beyond the one day after the ovulation marker day because that is the postovulatory infertile phase of any menstrual cycle by definition. It is noticeable though that both the baseline and non-baseline profiles exhibit repeatable postovulatory features that are consistent with known biological facts and are likely associated with the pulsatile release of progesterone from the corpus luteum (the postovulatory entity formed from the former dominant follicle). These postovulatory features may be of use in a future extension of the program; they may also be of use in a future extension of the applicability of the apparatus and method beyond that discussed here.

The structure of the data-interpretation program, as shown in Table 2, consists of numerous layers of routines within two blocks, i.e., Block I=Preparation for Interpretation and Block II=Interpretation of Today's Probe Data.

TABLE 2

BASIC ELEMENTS OF THE PROBE DATA INTERPRETATION PROGRAM

Block I. Preparation For Interpretation

1) Cycle day/initiation of measurement
2) Today's probe data
3) Inventory of data in present cycle

Block II. Interpretation Of Today's Probe Data

First decision: Single-shot (1A) or contextual diagnosis (1B)
If 1A, go to single-shot routine
If 1B, continue
Second decision: Postovulatory (2A) or not (2B)
If 2A, infertile - unless ovulation + 1 (fertile)
If 2B, continue
Third decision: Before long-term predictive peak (3A) or after long-term predictive peak (3B)
If 3A, infertile
If 3B, continue
Fourth decision: Before short-term predictive peak (4A) or at short-term predictive peak plus
1 day before (4B)
If 4A, infertile
If 4B, fertile
continue
Fifth decision: Assess reliability of interpretation as one of the following:
1. highly reliable diagnosis     fixed readout
2. moderately high reliability of diagnosis     "fast spelling" readout
3. moderately low reliability of diagnosis     "slowly spelled" readout
This decision is based on:
a) number of data points used as context for today's data interpretation
b) conception statistics for today's day of cycle
c) reproducibility of data upon optional repetition (if any)
d) amplitude of today's probe data with respect to thresholds
e) uncertainty, if any, about the day of cycle (first day setting)

The routines of the first block, Preparation, establish the information required for data interpretation: today's cycle day, today's measurement data, and the "inventory" of prior data, if any, from previous measurements in the present cycle as may be stored in the probe's memory.

The routines of the second block perform the actual interpretation: the process consists of making five decisions on whether today's probe measurement is consistent with infertile or with fertile interpretation and how reliable that diagnostic assessment is. The program looks for the much more frequent infertile diagnosis before looking to confirm fertile diagnosis, in the following systematic manner. First, it decides whether today is the first, so far the only, measurement in the present cycle which demands a "single-shot" diagnosis, or whether a contextual interpretation will be made possible by previously measured and stored data providing a context for today's data point and thus increasing the reliability of the interpretation. If contextual interpretation is made possible by previously stored data in memory, the second decision is whether the today's data point fits the characteristics of postovulatory data. If postovulatory, the interpretation is infertile unless the data fit the characteristics of ovulation marker+1 day (which requires the interpretation of fertile).

If the outcome of the second decision is not postovulatory data characteristics, the third decision is whether the data fits the characteristics of data before or after the first peak FP (the long-term predictive peak); if before, then the interpretation is infertile. If the outcome of the third decision is that the data point fits the characteristics of data after the first peak, the fourth decision is made on whether the data fits far enough before the second peak SP (also known as the short-term predictive peak) which means infertile or whether it fits at the second peak which means fertile. For the data point of today to fit at the second peak means that it corresponds to one of the characteristic features of the second peak as discussed below (Table 4): Either to SM or to SP or to OM, the three data points that define the peak.

In either case, the fifth decision follows to assess the reliability of either of the diagnostic conclusions (fertile or infertile). The reliability descriptor is one of three degrees: 1. High reliability, 2. Moderately high reliability, 3. Moderately low reliability. The reliability assessment is a function of several factors: a) the number of data points from this cycle's inventory that have been used for today's data contextual interpretation, b) the conception statistics for today's day of cycle referenced to the characteristic feature of the cyclic profile including the ovulation marker and the long-term predictive peak, c) the reproducibility of the measurement data if the user opts to repeat the measurement within the allowed two hours, d) the amplitude of today's probe data with respect to the fertility threshold and the ovulation threshold which in certain instances increases the reliability more than in others depending on day of cycle (e.g., data above 220 on day 9±1 increases the reliability of infertile interpretation), and e) the uncertainty, if registered, about the correctness of the day of cycle which may have arisen upon the initialization of the day of cycle counter (relative time clock) if the user forgot to do this on day 1 of the cycle (i.e., on the day of her first menstrual bleeding).

Each time the display of the intelligent probe is to indicate either "fertile" or "infertile" according to the flow diagrams in the figures below, the diagnostic interpretation is stored along with the raw data and a connection is made with the routine of the fifth decision (reliability assessment). A relatively high reliability of the diagnostic data interpretation is then indicated by a steady appearance of the fertility diagnosis on the LCD display, versus a relatively low reliability of the diagnostic data interpretation which is indicated by slow, letter by letter, emergence of the word "fertile" (or "infertile" as the case may be) on the display, in such a manner that the complete word never appears but rather the "spelling" is repeated at least twice. This focuses the user's mind on the fact that the diagnostic statement is relatively unreliable, although it is always more reliable than merely guessing the fertility status based on the day of cycle alone (as in the discredited so-called calendar or rhythm method of birth control). The only truly indeterminate situations, no better than the day-of-cycle based guess, arise from the discouraged possible use of the intelligent probe in the inadequate-context diagnostic mode such as in the single-shot diagnosis discussed below. The LCD display then indicates "unsure" or similar indication of indeterminate diagnostic interpretation. In recommended use, a moderately high reliability of the diagnostic interpretation of data is indicated by fast emergence, i.e., rapid spelling of the diagnostic outcome on the display, revealing the complete word ("fertile" or "infertile") for a brief moment before repeating the fast "spelling" procedure at least four times.

In summary, there is an unambiguous, easily intuitively understood distinction made between the different confidence levels of the diagnostic data-interpretation statements. Either diagnostic statement is available on the display for a limited period of time; if this turns out to be insufficient, the user can easily bring the result up again by simply pressing the "on" button 16 again.

With reference to the reliability decision about the confidence level of the diagnostic interpretation, the quality requirements of the conception statistics, particularly in terms of homogeneity of the data, must be emphasized. In so far as the reliability descriptor of the fertility status diagnosis is one innovation of this application, and in so far as the conception statistics are factored into the descriptor, this point is of utmost importance. The clinical trial, that will generate the data on the conception statistics with reference to the long-term predictive peak, is yet to be performed. The basic requirement of the trial must be the single-attempt requirement: The women participating in the trial will be required to make a single attempt at conception in the cycles they contribute to the trial. At least four cycles each will be required. The women will be divided into several groups that make single attempts at conception on different days of cycle after their long-term predictive peaks. In this manner, the probabilities of conception will be established statistically for individual cycle days, allowing for the tonic growth phase of the antral follicle. It is planned to finalize the design of the reliability assessment routine at that time.

The numerical values of the measurement data in Tables 3 to 5, just as those in the graph of FIGS. 10 to 12, pertain to the particular calibration of the particular preferred embodiment of the method and apparatus of the invention discussed in this patent application. The qualitative aspects of the probe profile features listed in Tables 3 to 5 similarly pertain to the particular embodiment of the apparatus and method utilized here for the purpose of teaching the invention. It is to be understood that the characteristic features of the cyclic profile depend on, and change with, the particular biological species to which the probe may be applied as well as with the waveform selected and, more generally, the characteristic features depend on and change with the mode of electrode excitation and the mode of monitoring. The data in FIGS. 10 to 12 and in Tables 3 to 5 are provided by way of examples, without prejudice to the scope of the invention.

TABLE 3

CHARACTERISTIC FEATURES OF THE PROBE CYCLIC PATTERN

POSTOVULATORY FEATURES

High day number (t > 17)
Day number may be 12 < t < 17 with data
d < 150
Low peak values (d < 200)
Later peaks are higher than earlier peaks
OVULATION MARKER Data amplitude approx. 95 (85 < d < 105)
Follows on two predictive peaks
Occurs only on days 12-17
PREOVULATORY FEATURES Low day number
Occur never after ovulation
High peak values (d > 200)
First minimum on day 7 ± 1
First minimum on day 8 for
otherwise on day 6
Second minimum on day 12 ± 2
First peak starts from day 7 ± 1
Second peak starts from day 12 ± 2
Two peaks only
short cycles,
Lone-term predictive peak features Starts from day 7 ± 1
Does not occur after ovulation marker
or after short-term predictive peak
If data goes x days up then it goes x ± 2 days down
High readings (d > 200)
Apex on day 9 or day 10
Short-term predictive peak features Starts from day 12 ± 2
Occurs after long-term peak
Does not occur after ovulation
Narrow width 1-3 days, mostly one day
Apexondayl1-15
Amplitude within a range Table 2 summarizes the structure and basic elements of the data-interpretation program. In the tabulated systematic manner, most diagnostic interpretations are made with a high degree of confidence, due to the high information content of the probe cyclic pattern. The high information content is summarized in Table 3 (Characteristic features of the probe cyclic pattern). The wealth of characteristic features allows certain diagnostic interpretations to be made more readily, and/or with a higher reliability of the diagnosis, than others. For example, ovulation marker is readily and reliably determined if all the conditions are satisfied as follows: today's reading is between 85 and 100 uA and two peaks have occurred beforehand with the features of the predictive peaks as listed in Tables 3, 4, and 5. In the case of the ovulation marker, the diagnosis is also quite reliable even if made in the absence of extended context information in the probe memory.

Table 4 lists the numerical details of the characteristic features of the second peak of the probe cyclic profile, also called the short-term predictive peak.

TABLE 4

CHARACTERISTIC FEATURES OF THE SECOND PEAK, SP (THE OVARIAN PEAK A.K.A. THE SHORT-TERM PREDICTIVE PEAK) SHOWN IN DATA-POINT COORDINATES t, d

| Cycle Number | BF | SM | SP | OM | $g_{up}$ | $g_{down}$ |
|---|---|---|---|---|---|---|
| A. BASELINE CYCLES | | | | | | |
| PM1 | 12, 158 | 13, 150 | 14, 211 | 1592 | 61 | 119 |
| PM2 | 13, 183 | 14, 150 | 15, 215 | 16, 100 | 65 | 115 |
| PM3 | 9, 235 | 10, 142 | 11, 218 | 12, 88 | 76 | 130 |
| B'aseline range | 9-13, 158-183 | 10-14, 142-150 | 11-15, 211-218 | 12-16, 88-100 | 61-76 | 115-130 |
| B. NON-BASELINE CYCLES | | | | | | |
| LK4 | 13, 135 | 13, 135 | 14, 158 | 17, 96 | 23 | 50 |
| LK5 | 13, 129 | 14, 128 | 15, 162 | 16, 95 | 34 | 67 |
| LK6 | 13, 178 | 14, 164 | 15, 220 | 16, 102 | 56 | 118 |
| Non-baseline range | 13, 129-178 | 13-14, 128-164 | 14, 15, 158-220 | 15-16, 95-108 | 23-56 | 50-118 |
| Overall range | 9-13, 129-183* | 10-14, 128-164 | 11-15, 158-220 | 12-16, 88-108 | 23-76 | 50-130 |

Key:
t = time [day of cycle],
d = probe data [microamperes],
BF = beginning of fertility window,
SM = second minimum,
SP = second peak,
OM = ovulation marker,
$g_{up} = d_{SP} - d_{SP-1}$,
$g_{down} = d_{SP} - d_{SP+1}$.
*Except for PM3 which is a short cycle with a short follicular phase and its BF therefore anomalously coincides with the apex of the first peak (which otherwise precedes BF by several days in cycles with longer follicular phases)

Table 4 is the list of the characteristics of the second peak that occurs within the window of fertility:
a) the start of the peak, i.e., the second minimum SM is within the range of cycle day 10 to 14 and its amplitude ranges from 128 to 164 uA;
b) the peak day coordinate of SP is within the range of cycle day 11-15 and the range of its amplitude coordinate is 158-220 uA;
c) the ovulation marker OM occurs within the day of cycle range 12-16 and its amplitude range is 88-108 uA;
d) the timing of the second peak of the non-baseline cycles does not deviate from the baseline range of the respective cycle days;
e) amplitude-wise, the deviation from baseline of the non-baseline range of probe measurement data is, as consistent with expectable estrogenic differences between baseline and non-baseline subjects, most pronounced at the peak's apex (downward) and least pronounced at the ovulation marker minimum which is reproducible within the narrow range noted under c) above;
f) the gradient of the ascending (gup) and of the descending (gdown) branches of the second peak SP are high in comparison to the top sections of the first peak. Where the non-baseline data are within the range of the first peak, they anticipate the short luteal phases of those cycles;
g) the beginning of fertility (BF) data are within the range of cycle day 9 to 13 and their amplitude ranges from 129 to 183 microamperes. This range excludes cycle PM3 which is a short cycle with a short follicular phase that causes a too high BF reading that lies, in fact, at the apex of the first peak. The anomalous first peak of cycle PM3 is a consequence of the short follicular phase which has clearly recognizable high gradients comparable with the high gradients of the second (fertile) peak;
h) the lowest second peak of the six (158 uA in cycle LK4) is associated with an unusually slow descent into the ovulation marker minimum.

TABLE 5

CHARACTERISTIC FEATURES OF THE FIRST PEAK, FP (THE DOMINANCE PEAK, A.K.A. THE LONG-TERM PREDICTIVE PEAK) SHOWN IN DATA-POINT COORDINATES t, d

| Cycle Number | FM | FP | BF | $g_{up}$ | $g_{down}$ | Cycle Length |
|---|---|---|---|---|---|---|
| A. BASELINE CYCLES ||||||||
| PM1 | 6, 158 | 10, 265 | 12, 158 | 25 | 45 | 28 |
| PM2 | 6, 182 | 9, 275 | 13, 183 | 15 | 20 | 30 |
| PM3 | 8, 128 | 9, 235 | 9, 235 | 107 | 93 | 26 |
| Baseline Range | 6-8, 128-182 | 9-10, 235-275 | 9-13, 158-183* | 15-25* | 20-45* | 26-30 |
| B. NON-BASELINE CYCLES ||||||||
| LK4 | 8, 137 | | 13, 135 | | | 26 |
| LK5 | 8, 138 | | 13, 129 | 12 | 25 | 24 |
| LK6 | | | 13, 178 | | | 28 |
| Non-baseline range | 8, 137-138 | | 12-13, 129-197 | 12 | 25 | 24-28 |
| Overall range | 6-8, 128-182 | 9-10, 235-275 | 9-13, 129-183* | 12-25* | 20-45* | 24-30 |

Key:
t = time [day of cycle],
d = probe data [microamperes],
FM = first minimum,
FP = first peak,
BF = beginning of fertility,
$g_{up} = d_{FP} - d_{FP-1}$,
$g_{down} = d_{FP} - d_{FP+1}$.
*Except for PM3 which is a short cycle with a short follicular phase and its FP day is therefore not infertile Table 5 lists the characteristics of the first peak FP, also referred to as the long-term predictive peak or the dominance peak:

a) The start of the peak, i.e., the first minimum FM, is within the range of cycle day 6 to 8 and its amplitude ranges from 128 to 164 uA.

b) Cycles shorter than 28 days have the FM on day 8 and therefore record the prior descent to the minimum whereas longer cycles have the FM on day 6 (meaning that the descent was completed during the menstrual bleeding period of days 1 through 5).

c) Comparing the amplitude range of the first minimum with the amplitude range of the BF data listed here as well as in Table 4 (from FIGS. 11 and 12) reveals that the BF range of amplitudes (beginning of fertility) is approximated by the range of the first minimum. The amplitude of the FM therefore anticipates the amplitude of the BF data. Provided that we exclude the short luteal phase cycles (that are distinguished by the steep gradients of the first peak), this finding can be used to identify the beginning of fertility BF on the day it occurs (in extended context-data interpretation), rather than identifying BF retrospectively from SM and SP data.

d) The peak day of FP is within the very narrow range of cycle days 9 or 10 and its amplitude is 200 uA and above.

e) The gradients $g_{up}$ and $g_{down}$ are low: excluding the short cycle PM3 because of its short follicular phase (associated with its anomalously narrow, low and sharp first peak), the gradients are distinctly lower than those of the second peak.

Figure 13:
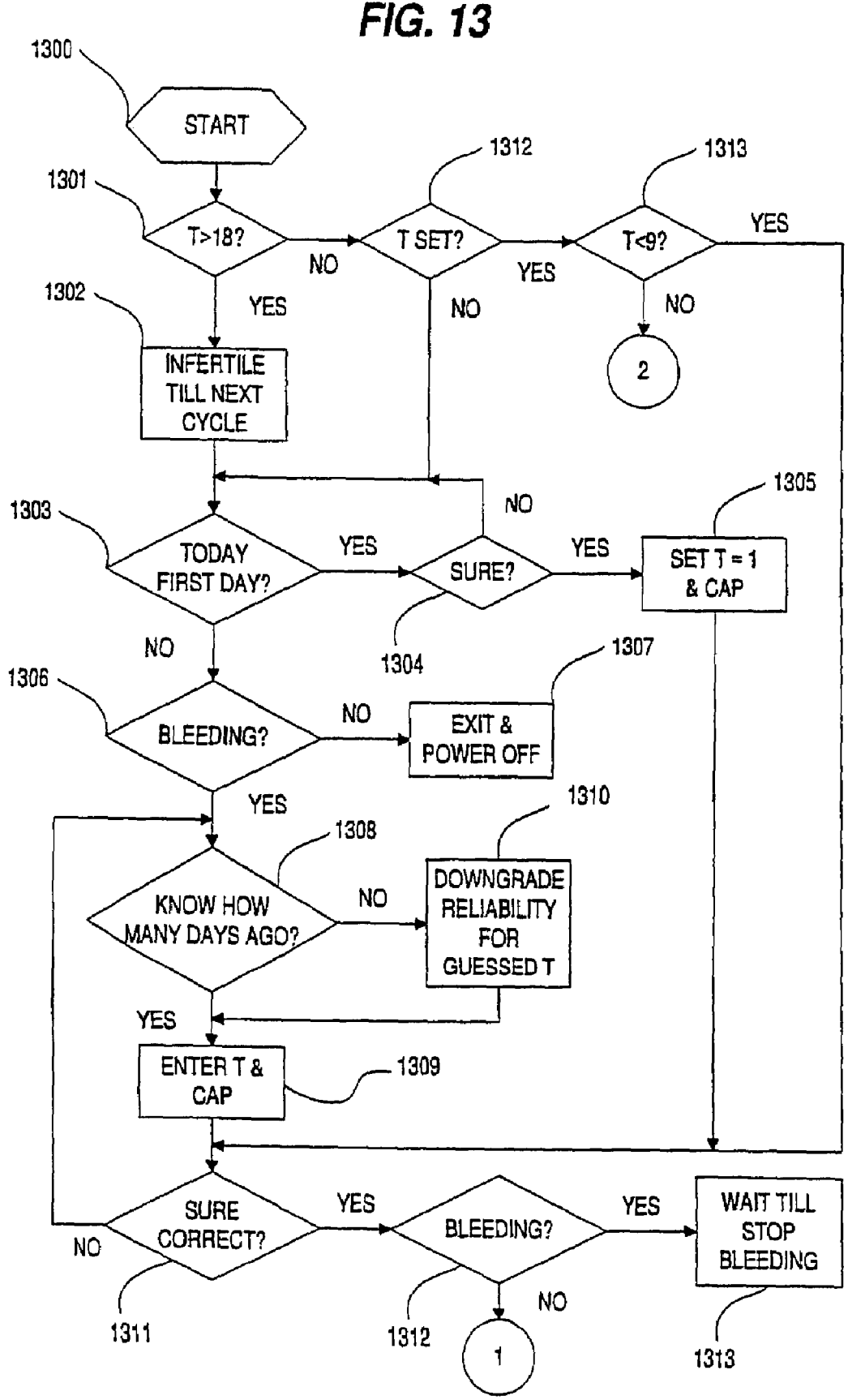
FIG. 13 is a flow diagram of the routine that performs the daily initiation of the intelligent probe measurement by examining or setting the day of cycle (relative time clock).

FIG. 13 is a flow diagram for the daily initiation of the diagnostic measurement, the main purpose of which is to examine and, if appropriate, to set the relative time clock that counts the days of cycle starting on the first day of menstrual bleeding. The routine is user-friendly in several ways. It allows the user to set day 1 retrospectively, if she forgets to do so on her first day of menstrual bleeding, although this causes a downgrade in the reliability assessment of any subsequent diagnostic interpretation of the data. The downgrading of the confidence level is more serious if the user forgets to set day 1 on day 1 and then only guesses how long ago day 1 was. However, since the shape of the cyclic pattern is more significant than the day of cycle alone, even this downgrade is not too serious in extended-context diagnosis. The user is asked to confirm the correctness of the day counter (relative time clock) setting in the first eight days of cycle, i.e., during the first three or so post-bleeding days, far from having to go through this interrogation every day.

The initiation of the daily measurement and its interpretation commences with START block 1300 and proceeds to inquire in block 1301 whether the relative time t (day of cycle) is greater than 18. This relative-time boundary condition of the fertile window is used here-by way of example within the frame of reference of the cyclic data in FIGS. 11 and 12. The particular numerical value of t=18 is used, rather than the general t=EF, with the proviso that its final numerical value, to be imbedded into the intelligent probe according to this invention, will depend on the outcome of the large-scale clinical trial invoked above in connection with the assessment of data-interpretation reliability in the discussion of Table 2. Therefore, the value to be adopted as the result of the clinical trial may be larger than 18. Clearly, should the "statistical extension" of this limit be too high, the program would be extended to rely on analysis of the shape of the postovulatory part of the cyclic profile rather than on a particular numerical value as adopted here.

Figure 14:
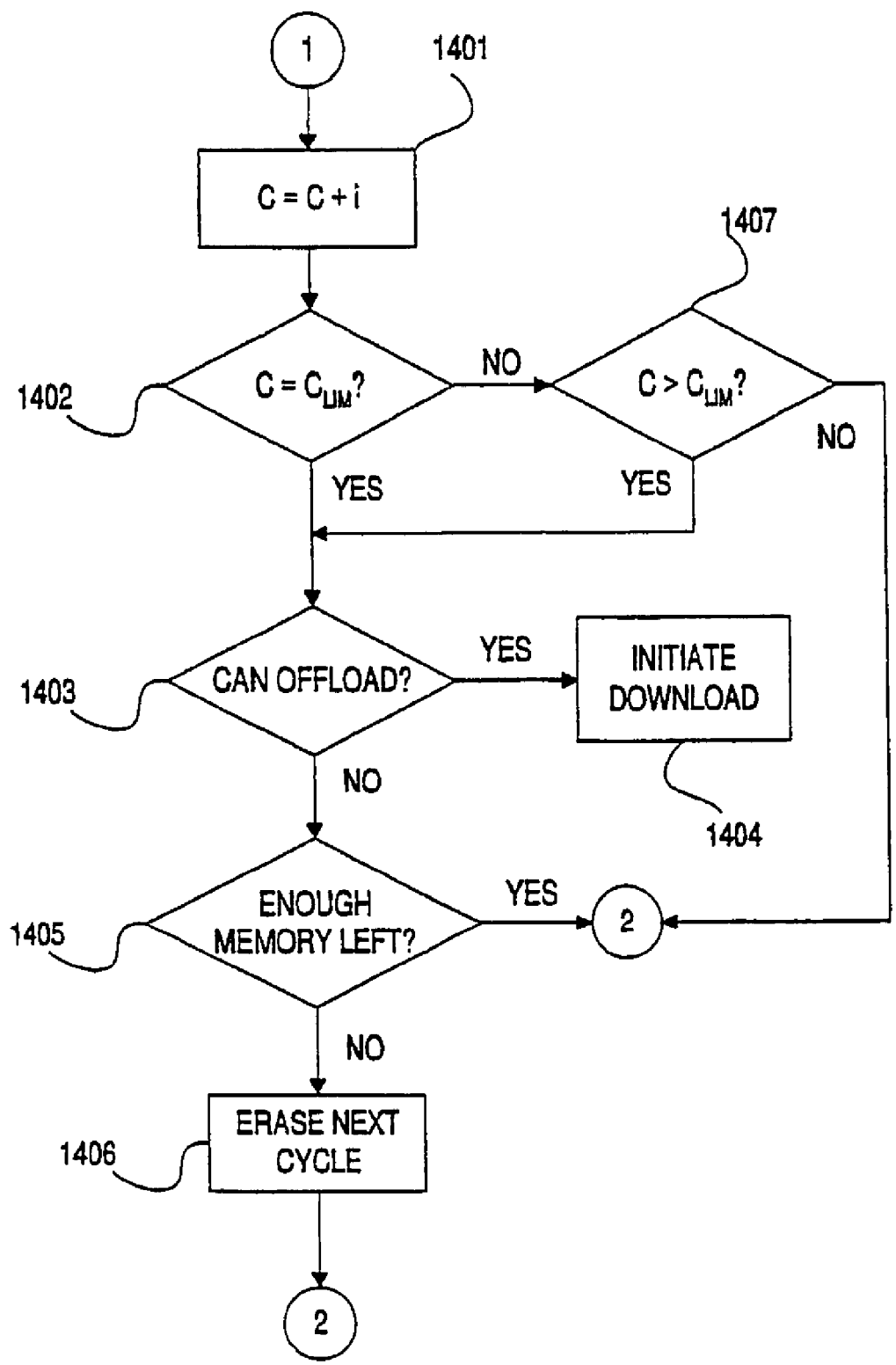
FIG. 14 is a flow diagram of a bookkeeping subroutine, within the initiation routine of FIG. 13, that checks the number of previously stored cycles against a preset limit and prompts the user to offload data once the limit has been reached and, if the user is not in a position to clear the memory, the subroutine makes room for the new cycle by erasing the oldest of the previously stored cycles.

If the day of cycle counter shows greater than 18, then block 1302 makes the interpretation of INFERTILE TILL NEXT CYCLE and displays this indication on the LCD display 17. Block 1303 then inquires whether today is the first day of the next cycle which the user judges by the presence or absence of menstrual blood flow. The confirm button 19 or, in another preferred embodiment, the positive side of control 18 is used to confirm the first day if blood is found to be present and to confirm this in response to block 1304 (SURE?). If not sure, the inquiry 1303 is repeated until a definitive answer is provided. If the response to 1303 is negative (by means of the negative side of control 18), then block 1306 inquires again whether bleeding and receives negative response causing exit and power off in block 1307. If bleeding is present even though today is not the first day, then block 1308 inquires into how many days ago. If known with certainty, then block 1309 allows the day number to be keyed in, using any or all three functions of control 18 (1, +, –, in any combination but logically starting with 1 and adding to it if more than one day). If not known for sure, block 1310 downgrades the reliability of the answer before proceeding to enter the less than certain number of days since bleeding started. Block 1309 also caps the count of days in the completed cycle (now "previous cycle") so as to eliminate any overrun due to the fact that the first day was not registered when bleeding actually started. These decisions are queried for correctness in block 1311 which allows for rectification of any mistakes by going again through the loop of the inquiry of block 1308, either with certainty (simply correcting a possible miskeyed answer in block 1309) or further downgrading reliability in block 1310. Confirmatory response to the SURE CORRECT? inquiry of block 1311 leads to another BLEEDING? inquiry of block 1312. This differentiates between the first five or so days when readings are obviated by menstrual bleeding (block 1313: WAIT TILL STOP BLEEDING) and the commencement of measurement in the new cycle for which the program goes into the routine of FIG. 14 via connector 1.

Returning to the first inquiry of this routine in block 1301, if the answer were negative, the next inquiry in block 1314 is as to whether relative time (cycle day register) has been set. If not, the just described loop beginning with query 1303 (TODAY FIRST DAY?) is entered. This allows for belated start of monitoring in the present cycle. The last element in this routine is the inquiry in block 1315 (t<9?) which, for practical reasons based on experience, gives the user another chance to make a correction of the day of cycle setting every day during the first three or 50 days after the cessation of menstrual blood flow. Since women know that these early days are infertile, some may be slack on the routine procedure and so this loop gives them a chance to rectify any mistakes due to belated start of the day of cycle counter.

Since this relative-time clock routine handles the initiation of new cycles, it must also handle the bookkeeping of previous cycles in relation to the memory space available for data storage. The flow diagram of this bookkeeping function is in FIG. 14 and it uses a counter of stored cycles, C, which is stepped up upon completion of the present cycle (i.e., the start of the next cycle, indicated by the start of menstrual bleeding). The design of the intelligent probe allows for a limited number, CLIM, of menstrual cycles to be stored, prompting the user to offload the stored data once the limit has been reached. One preferred limit is twelve menstrual cycles and this is based on the clinical definition of infertility which involves absence of conception after twelve months of unprotected intercourse; another preferred limit is six months which tends to prompt an earlier consultation with a physician if reduced fertility is a problem.

The bookkeeping aspect of this routine is based on continuous structure of the memory, such as a circular structure with a delineated point of first entry. The day of cycle, measurement and ancillary (e.g., cycle number intercourse registered, diagnosis and reliability) data for every day are stored in a continuous manner, including gaps should the user skip the daily measurement. Upon starting a new cycle by setting day 1 in the start-up routine depicted in FIG. 13 which connects with this bookkeeping routine via connector 1, the cycle counter C is stepped up in block 1401 and compared with the limit, CLIM, allowed for the number of stored cycles (block 1402). When the limit is reached, the user is prompted to offload the data (user instructions will recommend a physician's office visit in case of difficulty to conceive). The prompt to initiate the download is in block 1404 which is predicated by a positive response to the inquiry of block 1403 as to whether the woman has a capability to offload.

Even if she is not in a position to offload and thus renew the memory availability, the user is likely to have enough memory space left to continue, via connector 2, since allowance is made for long cycles (e.g., forty days long). Availability of memory space is queried in block 1405. In the absence of the offloading clearance, the memory will be filled up eventually and when the "not enough memory left" condition is detected in block 1405, the software erases, in block 1406, the oldest stored cycle data. This is where the continuance (e.g., circular or more likely rectangular layout) of the memory comes into play, so as to facilitate the erasure of the oldest data before the more recently stored data may be treated in the same manner, should the user continue using the probe without offloading. This design secures the availability of the most recent inventory or history of the woman's menstrual cycles even in the event of having exceeded the memory limit (whether it be six or twelve or any other number of previously stored cyclic profiles).

The fact that the intelligent probe can never refuse to perform the daily measurements on account of an over-filled memory is an important and essential aspect of its user-friendly design. It is to be highlighted, however, that for the many near-stereotypical cycles of around 28 days in cycle length, there is an approximately 30% spare memory space available because of the allowance for approximately 30% longer cycles in the setting of the limit CLIM. The greater the number of cycles allowed to be stored (GuM), the greater the favorable impact of this design feature. All the stored data, including the "extra" cycles are accessible for offloading and downloading. The remaining element in this routine is block 1407 which is a bookkeeping inquiry into whether the data is overflowing the memory limits (handled as discussed above) or whether it is still below the CLIM in which case the program goes to the next routine.

Figure 15:
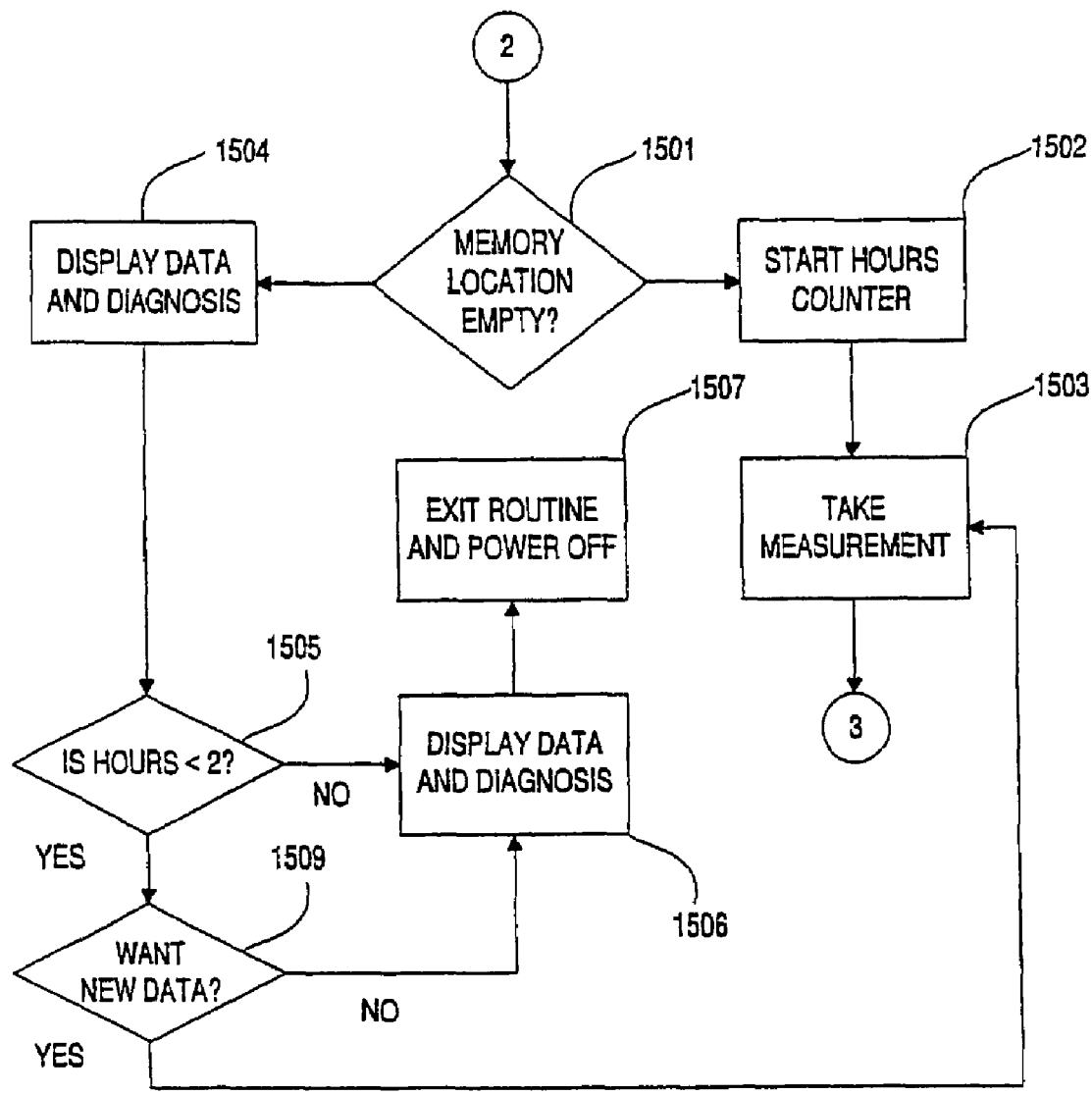
FIG. 15 is a flow diagram of the routine that performs the measurement.

FIG. 15 is a flow diagram of the routine that performs the actual measurement once the time coordinate has been ascertained. This routine is again user-friendly in that it allows the user to repeat her daily measurement should she feel compelled to do so within two hours of first use. (The time of daily measurements is a personal choice and the user instructions advocate to adhere to the selected time of day, give or take an hour.) Any new measurement data for today is written over the data stored in today's memory location within the allowed two hours. A comparison with the previous data of today, if any, is made because the reproducibility of the measurement data, in case of more than one measurement, becomes a factor for the reliability (confidence level) of diagnosis assessment in the fifth decision of the data-interpretation program (not shown). The routine charted in FIG. 15 also performs the task of optionally repeating the display of today's fertility diagnosis, whether the user wishes to merely check the status or whether she wishes to repeat the measurement within the allowed two hours of the first measurement of the day.

The routine starts with an inquiry in block 1501 as to whether today's memory location is still empty in which case block 1502 starts the ancillary hours counter just before block 1503 takes the actual measurement (instructing the microprocessor 507 to actuate the electrodes 501 and 502, and to record the response; the instructions are not shown). If the memory location is not found empty by block 1501, block 1504 instructs the microprocessor to display the data from today's memory location and then the diagnostic interpretation of that data. After a brief period of time, sufficient for user's assessment of the displayed information, block 1505 tests the hours counter that had been started in block 1502 and, if the time elapsed is within the two hours allowance of the first measurement of today, block 1509 allows the user to repeat the measurement by means of block 1503. If the elapsed time is beyond the two hour limit introduced at block 1505 or if the user does not wish to repeat the measurement in block 1509, the previous data and diagnosis of today's fertility status are displayed again in block 1506 after which, following again a suitable delay for user's contemplation, the routine is exited and the intelligent probe is powered off in block 1507.

Figure 16A:
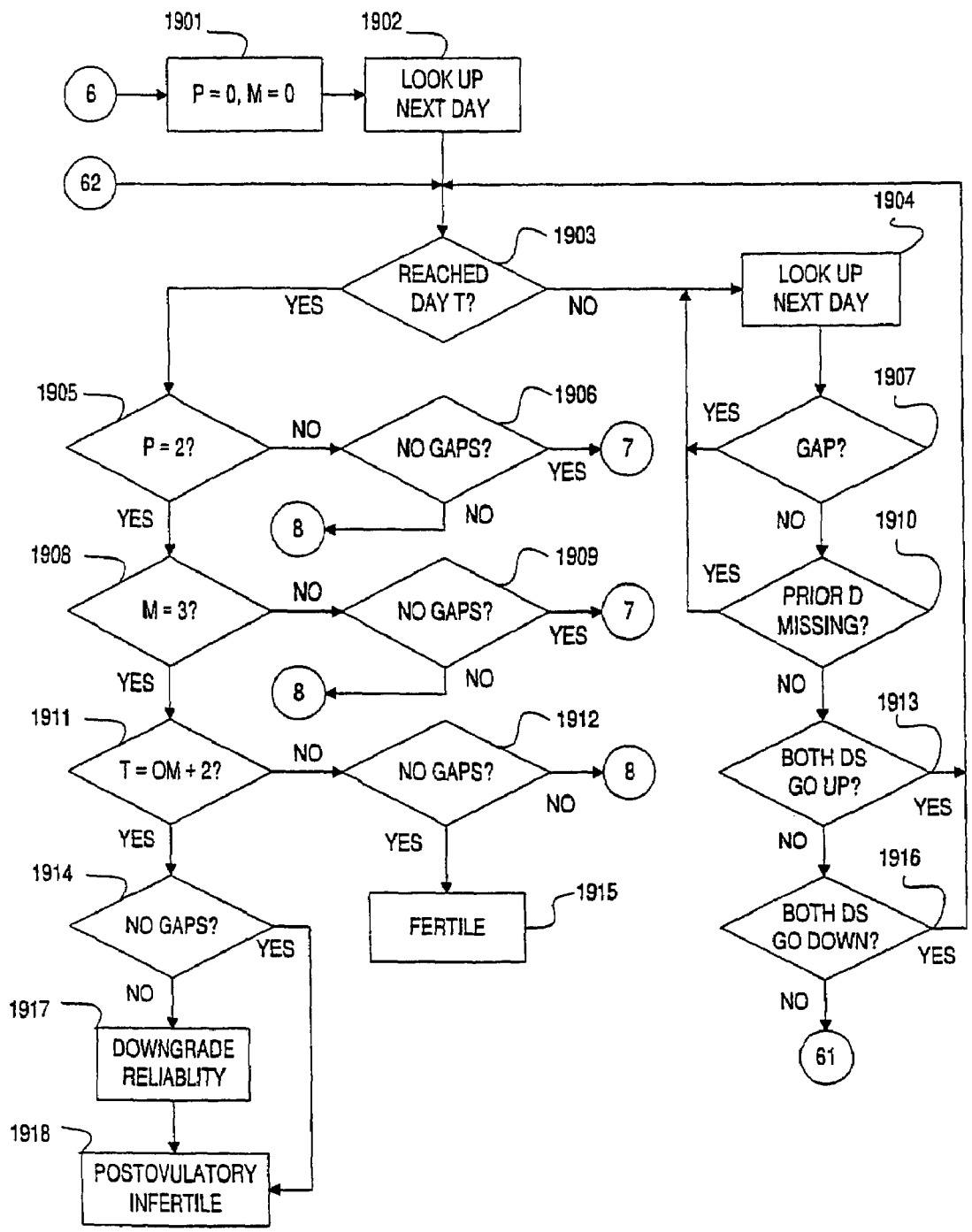
FIGS. 16A and 16B provide flow diagrams of the routine performing the second decision which is whether today's data is post-ovulatory infertile (after end of fertility EF) or not.

Returning to the preferred extended-context mode of data interpretation, FIG. 16A is a flow diagram of the routine that makes the decision, whether the data taken today is postovulatory infertile (i.e., after the EF boundary of the window of fertility), or not. The routine starts the examination of this cycle's inventory of data on the earliest day available in C memory (preferably day 6 or earlier), having initialized the counters of peaks and minima by means of which it looks for the postovulatory condition. The postovulatory condition is defined by having found in the inventory of the present cycle, prior to today's data, two peaks and three minima, all complying with the characteristics of the two predictive peaks and the associated minima, plus the day of cycle coordinate must correspond to two days after the third minimum which is the ovulation marker. The characteristics that this routine refers to are those listed in Tables 4 and 5 (numerical ranges of respective coordinates). As pointed out in the discussion of Tables 4 and 5 above, these characteristics pertain to the particular calibration and, more generally, to the particular mode of electrode excitation and the mode of monitoring in the particular embodiment of the apparatus and method of the invention.

Figure 16B:
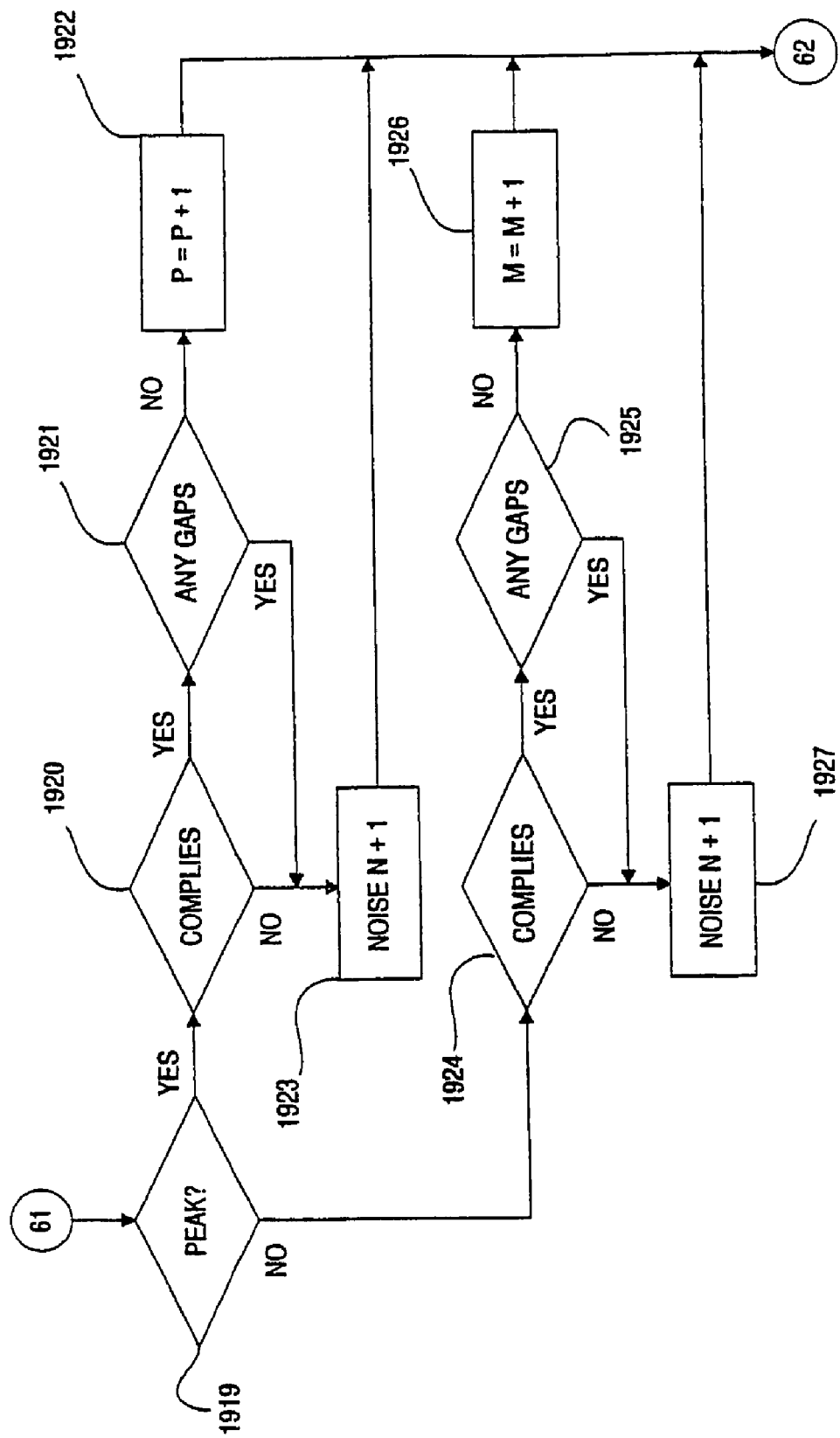

The decision routine is written out in two parts, FIGS. 16A and 16B, because of its length and complexity. The chief reason for the complexity is the possibility of gaps in the flow of data, should the user skip some daily measurement(s) and the possible occurrence of noise in the data. Both these complications are present in the examples of non-baseline cyclic profiles in FIG. 12. The second part of the routine in FIG. 16B re-defines as noise any lack of compliance of a detected peak or minimum with the characteristic features of the follicular phase of the profile. This is then recognized in the subsequent routines of the third and fourth decisions as a factor for downgrading the reliability of the diagnostic interpretation of the data.

The first element of the routine, block 1901, clears out the peaks and minima counters and the second, block 1902, instructs the microprocessor to seek or look up next day data (it has just found the earliest data of this cycle in the preceding routine). The third block, 1903, inquires as to whether the search has reached today's date yet and if so, the peaks and minima counters are interrogated, in succession, in blocks 1905 and 1908, respectively, as is the condition of today's day of cycle t (T=OM +2?) in block 1911. The subsequent steps are identical for all the three inquiries of blocks 1905, 1908 and 1911 if the answers are negative: blocks 1906, 1909 and 1912, respectively, inquire whether no gaps were found; if so, the program goes into the routine of the third decision (FIG. 17) whereas if the answer is negative since gap(s) found, the program goes into the fourth decision routine (FIG. 18).

Figure 17:
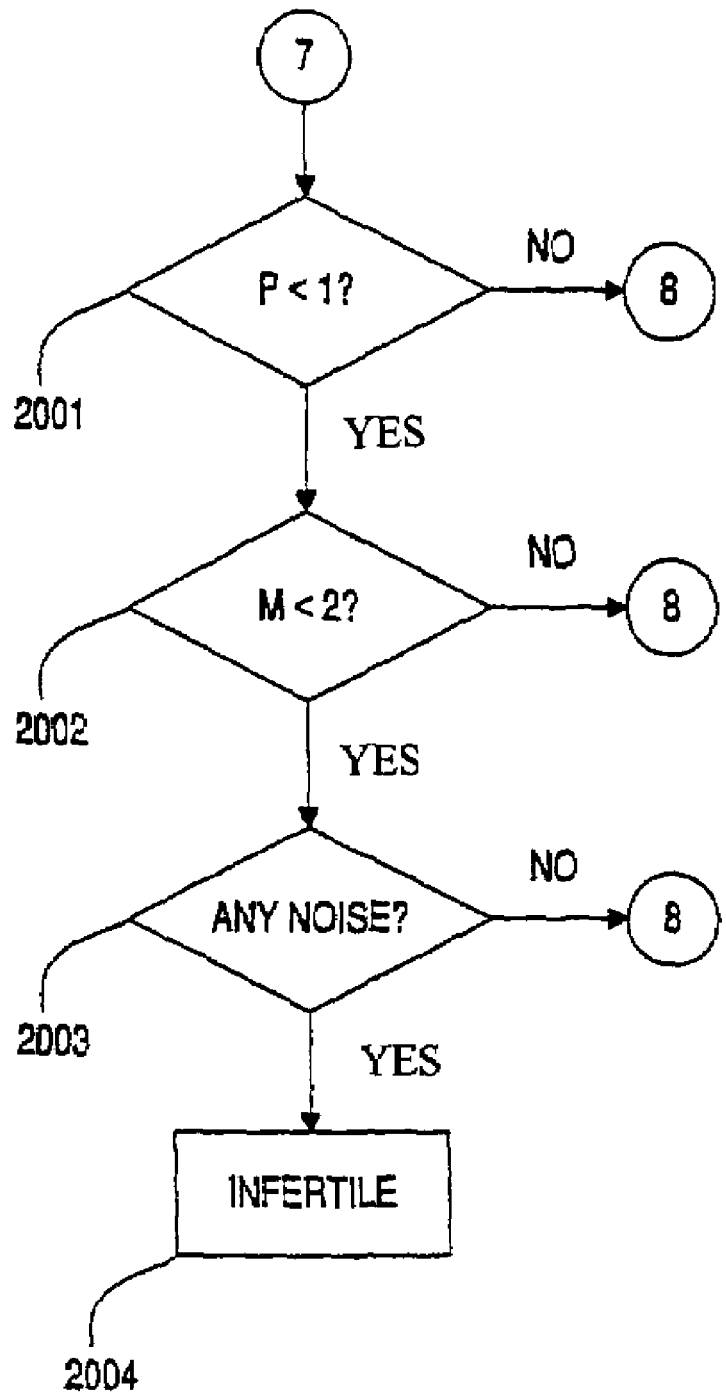
FIG. 17 is the routine of a decision as to whether the data of today fits before the first peak (also referred to as the long-term predictive peak) and means therefore infertile diagnosis, or whether it fits at or after the first peak.

FIG. 17 is a flow diagram of the routine that makes the decision if the outcome of the previous, second decision in FIG. 16A was "not postovulatory". The decision is whether the data fits before the first peak which means infertile diagnosis, or whether the data fits at or after the first peak. The condition of before the first peak is P=0 and M=1 (registers P and M count the peaks and minima, respectively) and it translates as infertile. If the condition is not satisfied (i.e., more than one minimum and at least one peak have been found), the fourth decision is to be made next.

Figure 18:
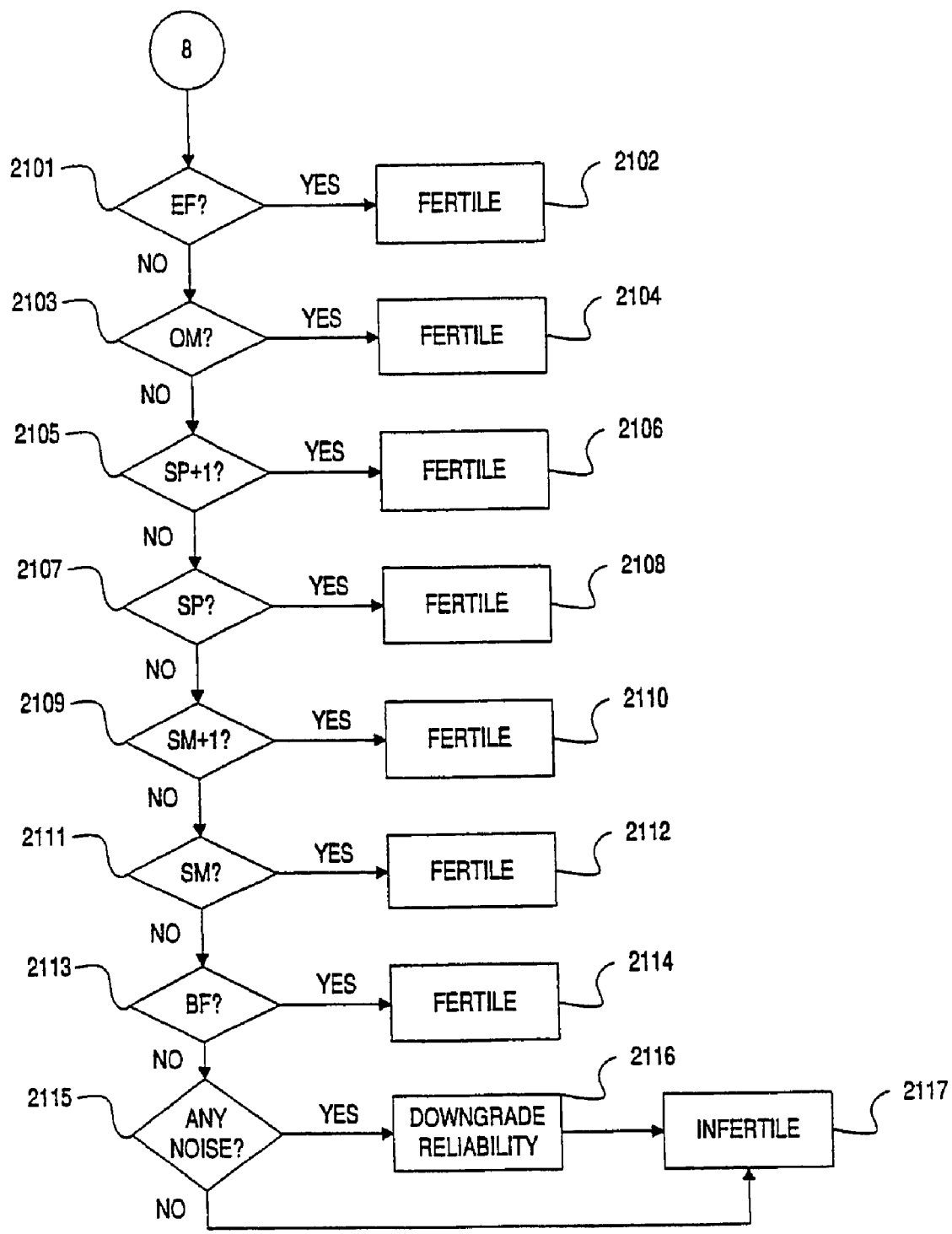
FIG. 18 is the routine of the decision as to whether the data fits well before the second peak, meaning infertile, or whether it fits at the second peak SP (also referred to as the short-term predictive peak) or one day before, which is the beginning of fertility BF, or one day after, which is the end of fertility EF.

FIG. 18 is a flow diagram of the routine of the decision which must be made if the outcome of the previous decision was "not before the first peak". The decision is whether the data fits well before the second peak or at any of the five points of the fertility window: the three points that define the second peak or one day before the "foot" of the peak which means one day before the second minimum, meaning the beginning of fertility BF, or one day after the ovulation marker (i.e., the third) minimum, meaning the end of fertility EF. The conditions queried in the decision routine of FIG. 18 have been dealt with earlier and the fertility window has also been defined. End of fertility EF−OM +1 (end of fertility is defined as one day after ovulation marker OM). Ovulation marker OM=d<OT (ovulation threshold) & P=2 (ovulation marker is defined by measurement data below the ovulation threshold and the peak counter registering two peaks). Second peak SP is defined by P>1 & M=2 & 155<d<225 & 10<t<16. Second minimum SM is defined by M=1&P=1 & 125<d<165 & 9<t<15. Beginning of fertility BF is defined by M=1 & P=0 & 125<d<240 & 8<t<14 or BF is defined by M=1 & P=1 & d.sub.BF=d.sub.FM+−10. This is where the characteristic features of the first and second peaks come into play and the program looks them up just like the human expert does: namely in a list such as those in Tables 4 and 5.

The second part of the routine of the decision described in FIG. 16B above is also important for another reason in addition to that discussed above. The compliance queries therein are also the points where aberrant features of a qualitatively deviant cyclic profile are discerned and separated from the merely quantitative deviations such as those exemplified by the data in FIG. 12. This separation is achieved by providing to the program another set of characteristic features that belong to another type of cyclic profile.

Figure 19:
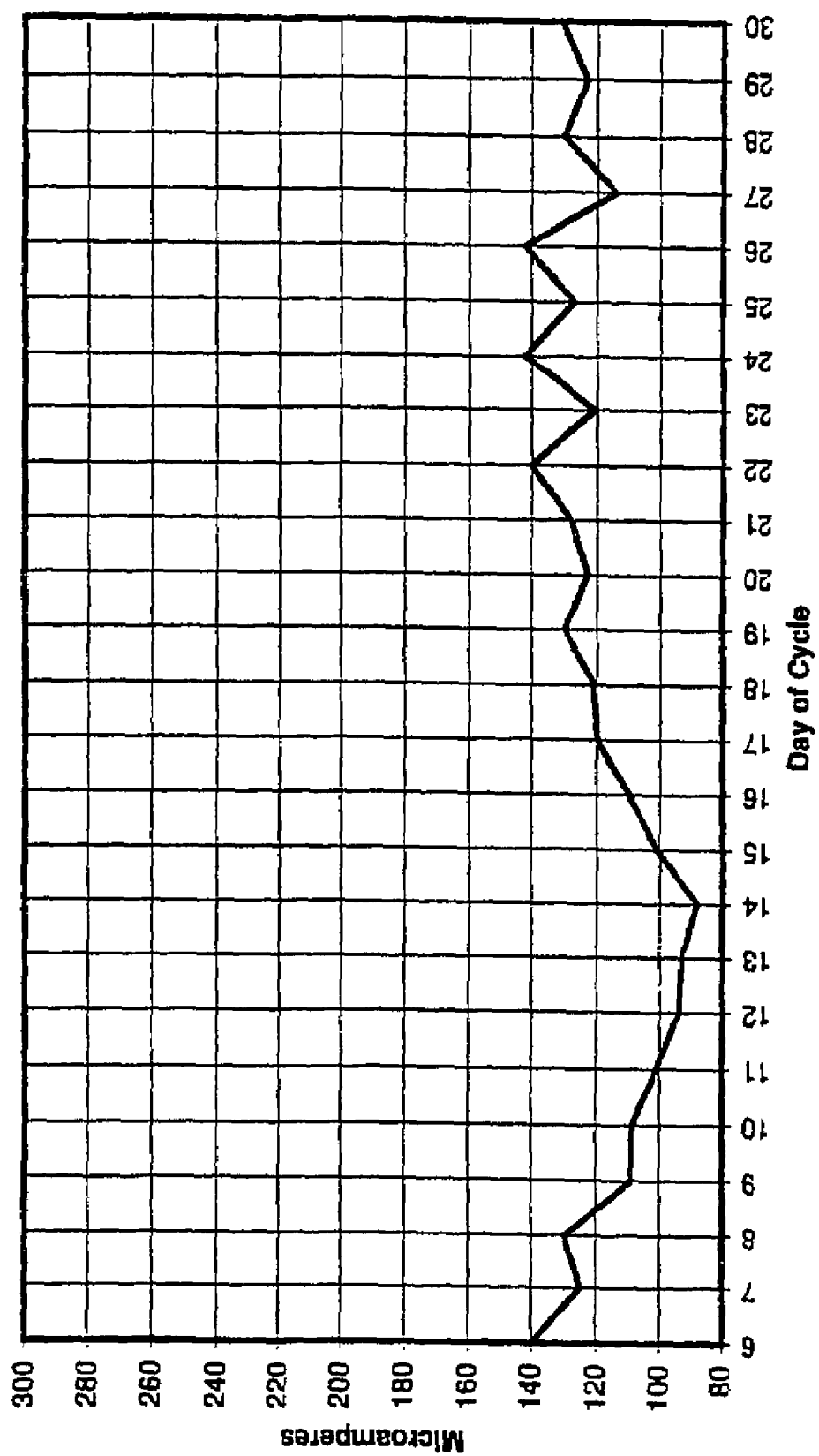
FIG. 19 depicts the probe cyclic profile of an aberrant cycle due to an apparent luteal phase defect (LPD).

An example of an aberrant cyclic profile is shown in FIG. 19 depicting a case of an aberrant luteal phase defect (LPD) which occurred m a perfectly healthy, 25 year old woman. This defect, a frequent cause of failure to conceive, is characterized by a complete absence of the first and second peaks. This means that the telltale signs of the reproductive system preparing for ovulation, by going through the stages of folliculogenesis as described above, are completely absent in this aberrant cyclic profile. As such, this qualitative deviation from the classical or baseline profile is readily characterized for recognition by the intelligent probe's microprocessor. The diagnostic indication throughout the cycle is "infertile-LPD". Both the woman-user and her physician have the benefit of early recognition (by day 10) of the defect, a significant benefit in the context of infertility management.

What is claimed is:

1. A method for diagnosing fertility status in a female mammal comprising the following steps:
   a. monitoring folliculogenesis of said female mammal by means of a fertility probe which generates ovarian function data;
   b. correlating said ovarian function data to a probe cyclic pattern generated by said fertility probe in response to said monitoring,
   wherein said probe cyclic pattern includes a first peak and a second peak which occur in said probe cyclic pattern prior to an ovulation marker, wherein said first peak includes an ascending part which begins at a first minimum and a descending part which ends at a second minimum, and wherein said apex of said first peak has the greatest amplitude in said probe cyclic pattern;
   c. defining within said probe cyclic pattern a portion of said descending part of said first peak between an amplitude about equal to said first minimum of said first peak and an amplitude about equal to said second minimum of said first peak; and
   d. predicting an occurrence of a fertile window based upon the portion which occurs prior to the ovulation marker.

2. The method of claim 1, further comprises the step of correlating said ovarian function data with said part of said probe cyclic pattern which includes said second peak having an ascending part which begins at said second minimum and a descending part which ends at an ovulation marker correlating with the point of least amplitude in said probe cyclic pattern.

3. The method of claim 2, further comprising the step of correlating said ovarian function data with said part of said probe cyclic pattern which includes post-ovulation peaks having an ascending part which begins at said ovulation marker, and wherein said fertility window ends upon correlation of said ovarian function data with said post-ovulation peaks for a period of about 24 hours.

4. The method of claim 3, wherein said step of monitoring folliculogenesis of said female mammal by means of a fertility probe which generates ovarian function data, further comprises the step of locating at least one of two electrodes to engage the cervical epithelium in the posterior fornix region of the vagina.

* * * * *